United States Patent [19]

Gross et al.

[11] Patent Number: 5,721,347
[45] Date of Patent: Feb. 24, 1998

[54] ESTERS AND AMIDES OF SUBSTITUTED PYRROLE ACETIC ACIDS

[75] Inventors: Paul Gross, Stockton, Calif.; Klaus Brendel, Tucson, Ariz.; Rifat Pamukcu, Cincinnati, Ohio

[73] Assignees: Cell Pathways, Inc., Aurora, Colo.; University of Arizona, Tucson, Ariz.

[21] Appl. No.: 491,101

[22] Filed: Jun. 16, 1995

Related U.S. Application Data

[63] Continuation of Ser. No. 245,060, May 17, 1994, abandoned, which is a continuation of Ser. No. 95,310, Jul. 21, 1993, abandoned, which is a continuation of Ser. No. 777,452, Oct. 11, 1991, abandoned, which is a continuation-in-part of Ser. No. 609,891, Nov. 6, 1990, abandoned.

[51] Int. Cl.$^6$ ............... C08B 37/08; C08B 15/00; C07D 207/00; A61K 38/00
[52] U.S. Cl. ............... 536/20; 536/56; 548/400; 530/300
[58] Field of Search ............ 536/20, 56; 548/400; 530/300

[56] References Cited

U.S. PATENT DOCUMENTS

| | | | |
|---|---|---|---|
| 3,161,654 | 12/1964 | Shen | 260/319 |
| 3,576,800 | 4/1971 | Yamamoto et al. | 260/340 |
| 3,752,826 | 8/1973 | Carson | 260/326.3 |

OTHER PUBLICATIONS

Waddell, W.R., et al., J. Surg. Oncol., vol. 24, pp. 83–87 (1983).
Waddell, W.R., et al., Am. J. Surg. vol. 157, pp. 175–179 (1989).
The Merck Index Therapeutic Category & Biological Activity Index pp. 15–16 (1989).
Martindale, The Extra Pharmacopoeia (1989).
Bayer, B.M., et al., J. Pharmacol. Exp. Ther., vol. 210, No. 1, pp. 106–111 (1979).
Bayer, B.M., et al., Biochem. Pharm., vol. 28, pp. 441–443 (1979).
Patrice, T., et al., Dig. Dis. & Sci. vol. 34, No. 11, pp. 1681–1685 (1989).
Pollard, M., et al., Cancer Treat. Rep. vol. 64, pp. 1323–1327 (1980).
Narisawa, T., et al., Gann., vol. 73, pp. 377–381 (1982).
Narisawa, T., et al. Cancer Res., vol. 41, pp. 1954–1957 (1981).
Rubio, C.A., et al. Dis. Colon Rectum, vol. 32, pp. 488–491 (1989).
Hucker, H.B. et al., J. Pharm. & Exp. Therap., vol. 153, No. 2, pp. 237–239 (1966).
Stedman's Medical Dictionary, 24th Edition, p. 1120 (circa 1989).
Harrison's Principles of Internal Medicine, Seventh Edition, pp. 1492–1493 (circa 1977).

*Primary Examiner*—John Kight
*Assistant Examiner*—Everett White
*Attorney, Agent, or Firm*—Brinks Hofer Gilson & Lione

[57] ABSTRACT

Esters and amides of substituted pyrrole acetic acids are useful in the treatment of colonic polyps.

31 Claims, No Drawings

ESTERS AND AMIDES OF SUBSTITUTED PYRROLE ACETIC ACIDS

This application is a continuation of Ser. No. 08/245,060 filed May 17, 1994, now abandoned; which is a continuation of Ser. No. 08/095,310 filed Jul. 21, 1993, now abandoned; which is a continuation of Ser. No. 07/777,452 filed Oct. 11, 1991, now abandoned; which is a continuation-in-part of Ser. No. 07/609,891, filed Nov. 6, 1990, now abandoned.

TECHNICAL FIELD

This invention relates to compositions and methods for treatment or prevention of colonic polyps.

BACKGROUND OF THE INVENTION

Each year in the United States alone, approximately 60,000 people die from colon cancer, and over 150,000 new cases of colon cancer are diagnosed. For the American population as a whole, individuals have a six percent lifetime risk of developing colon cancer, making it the second most prevalent form of cancer in the country. Colon cancer is also prevalent in Western Europe.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure, because most victims do not experience symptoms until the disease is advanced.

The incidence of colon cancer increases with age, particularly after the age of 40. Since the mean ages of populations in America and Western Europe are increasing, the prevalence of colorectal cancer should increase in the future.

In view of these grim statistics, efforts in recent years have concentrated on colon cancer prevention. Colon cancer usually arises from pre-existing benign growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

As indicated above, each polyp carries with it a chance that it will develop into a cancer. The likelihood of cancer is diminished if a polyp is removed. However, many of these patients demonstrate a propensity for developing additional polyps in the future. They must, therefore, be monitored periodically for the rest of their lives for polyp reoccurrence.

In most cases (i.e. the cases of so-called common sporadic polyps), polyp removal will be effective to reduce the risk of cancer. In a small percentage of cases (i.e. the cases of the so-called polyposis syndromes), removal of all or part of the colon is indicated. The difference between common sporadic polyps and polyposis syndromes is dramatic. Common sporadic polyp cases are characterized by relatively few polyps, each of which can usually be removed leaving the colon intact. By contrast, polyposis syndrome cases can be characterized by many (e.g. hundreds or more) of polyps—literally covering the colon in some cases, making safe removal of the polyps impossible short of surgical removal of the colon. Because each polyp carries with it the palpable risk of cancerous development, polyposis syndrome patients invariably develop cancer if left untreated. Many of these patients have undergone a severe change in lifestyle as a result of surgery. Patients have strict dietary restrictions, and many must wear ostomy appliances to collect their intestinal wastes.

Recently, several non-steroidal anti-inflammatory drugs ("NSAIDs"), originally developed to treat arthritis, have shown effectiveness in inhibiting and eliminating polyps. Polyps virtually disappear when the patient take the drug. However, the prophylactic use of currently available NSAIDs, even in polyposis syndrome patients, is marked by severe side reactions that include gastrointestinal irritations and ulcerations. Once NSAID treatment is terminated due to such complications, the polyps return, particularly in polyposis syndrome patients.

SUMMARY OF THE INVENTION

This invention is a novel class of compounds of formula I below that are effective in eliminating and inhibiting polyps, but are not characterized by the severe side reactions of NSAIDs.

This invention also relates to a method of treating patients with common sporadic polyps and polyposis syndromes to reduce or eliminate their polyps by administering to a patient in need of such treatment a physiologically effective amount of a compound of formula I.

DETAILED DESCRIPTION OF THE INVENTION

As discussed above, the present invention is a class of compounds of formula I below for treating individuals with common sporadic polyps and polyposis syndromes:

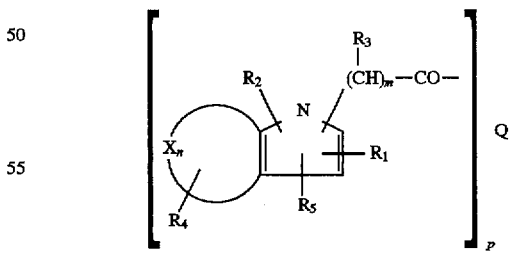

wherein n is 0 or 1 and X represents a condensed phenyl ring;

one of $R_1$ and $R_2$ is independently selected from the group consisting of hydrogen, halogen, lower alkyl; and the other of $R_1$ and $R_2$ is independently selected from the group consisting of substituted or unsubstituted phenyl, benzyl, thienyl, napthyl, pyridyl, furyl, biphenyl, benzoyl, cinnamoyl, thienylcarbonyl, napthylcarbonyl, pyridylcarbonyl, furylcarbonyl or biphenylcarbonyl wherein said substituents are selected from the group consisting of amino, halogen, lower alkyl, lower alkylthio, lower alkoxy or lower haloalkyl;

m is an integer from 1 to 3;

$R_3$ is selected from hydrogen and lower alkyl, or one or more of hydrogen and lower alkyl when m is greater than 1;

$R_4$ is one or more members of the group consisting of hydrogen, lower alkyl, alkoxy, haloalkyl, alkylthio, and halogen;

p is an integer of at least 2;

Q is the depronated residue of a polymer or macromolecular structure having at least two primary and/or secondary amines and/or hydroxy groups; and When n is 0, the structure in formula I represents a substituted pyrrole ring, and $R_5$ is selected from the group consisting of hydrogen, lower alkyl, alkoxy, alkylthio, and halogen. When n is 1, the structure in formula I represents a substituted indole ring.

As used herein, the term "halo" or "halogen" refers to chloro, bromo, fluoro and iodo groups, and the term "alkyl" or "alkoxy" refers to straight, branched chain or cyclic groups. The term "lower alkyl," "lower alkoxy" or "lower alkylthio" refers to groups containing from 1–5 carbon atoms.

This invention is also a method of treating patients with colonic polyps to reduce the polyps by administering to such a patient a therapeutically effective amount of a compound of Formula I wherein $R_1$–$R_5$, m, X, n, and p are as defined above, but Q is the deprotonated residue of a polyamino or polyhydroxy compound.

Compounds of Formula I may be formulated into compositions together with pharmaceutically acceptable carriers for parenteral injection, for oral administration in solid or liquid form, for rectal administration, and the like, although oral administration is most preferred.

Compositions according to the present invention for parenteral injection may comprise pharmaceutically acceptable sterile aqueous or nonaqueous solutions, suspensions or emulsions. Examples of suitable nonaqueous carriers, diluents, solvents or vehicles include propylene glycol, vegetable oils, such as olive oil, and injectable organic esters such as ethyl oleate. Such compositions may also contain adjuvants such as preserving, wetting, emulsifying and dispersing agents. They may be sterilized, for example, by filtration through a bacteria-retaining filter, or by incorporating sterilizing agents into the compositions. They can also be manufactured in the form of sterile solid compositions which can be dissolved in sterile water, or some other sterile injectable medium immediately before use.

Solid dosage forms for oral administration include capsules, tablets, pills, powders, troches and granules. In such solid dosage forms, the active compound is admixed with at least one inert diluent such as sucrose, lactose or starch. Such dosage forms can also comprise, as is normal practice, additional substances other than diluents, e.g., lubricating agents such as magnesium stearate. In the case of capsules, tablets, troches and pills, the dosage forms may also comprise buffering agents. Tablets, pills and granules can additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Compositions for rectal administration are preferably suppositories which may contain, in addition to the active substance, excipients such as cocoa butter or a suppository wax.

Actual dosage levels of active ingredient in the compositions of the invention may be varied so as to obtain an amount of active ingredient effective to achieve polyp-eliminating activity in accordance with the desired method of administration. The selected dosage level therefore depends upon the nature of the active compound administered, the route of administration, the desired duration of treatment, and other factors. If desired, the daily dose may be divided into multiple doses for administration, e.g. two to four times per day.

Compounds of this invention can be made by one of the five general schemes below.

SCHEME I

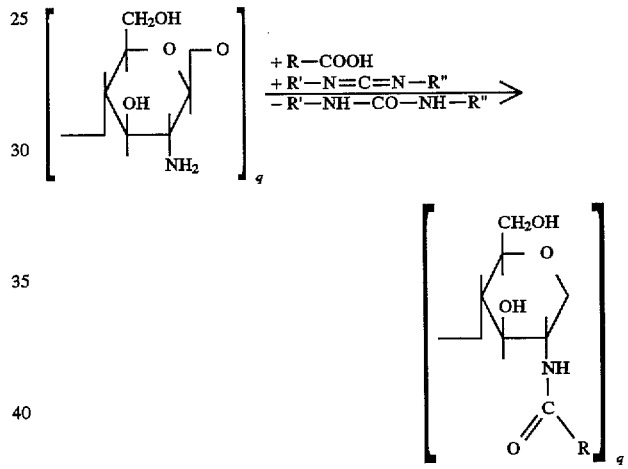

This scheme is useful for cases, where Q is a water swellable polymer carrying aminogroups. The water soluble carbodiimide allows acylation in the alcoholic-aqueous phase, and the water soluble by-product urea can be removed by water, from the acylated polymer. The scheme allows acylation with carboxylic acid sensitive to the conditions of acid chloride or acid anhydride formation.

A chitosan gel $(GlcN)_q$ is prepared from chitosan, according to the method of S. Hirano et al. (Carbohyd. Res. 201 (1990) pp. 145–149) where q is the number of repeating units within the chitosan molecule. The gel is stirred in 70% aqueous methanol solution, at 0°–5° C., with the R-carboxylic acid (2 equivalents per GlcN; where R is the group in the brackets in formula I minus the attached carbonyl), and with a water-soluble carbodiimide (R'—N=C=N—R"; 2 equivalents per GlcN) for three days. (R' and R" are cycloalkyl or alkyl, or the like, containing also quaternary ammonium or sulfonate salt for solubilization of the carbodiimide.) The resulting gel is homogenized, washed well with distilled water, stirred with NaOH (1.2 equivalents per GlcN) in water (50 ml per g of chitosan) for five days. The mixture is homogenized and washed to neutrality. The gel is then dried to an amorphous powder.

SCHEME II

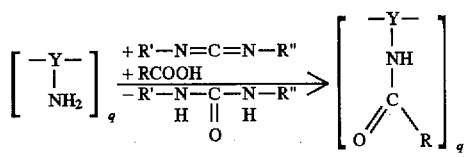

This scheme is useful for cases, where a salt between R—COOH and a polyamine Q is swellable or soluble in DMF. The carbodiimide is chosen, so that the by-product urea is soluble in dichloromethane, and therefore removable by extraction with it. Sodium hydroxide is used to extract unreacted R—COOH, so this scheme is useful for cases where acylation is difficult and incomplete. The scheme especially allows acylation with carboxylic acids that degrade under the conditions of acid chloride or acid anhydride formation.

$(GlcN)_q$ "chitosan," polylysine or similar polyamine "Y" (0.01 mol-$NH_2$ groups; where q is the number of repeating amino-containing units per molecule of polyamine) are rapidly stirred in dimethylformamide ("DMF," 30 ml) at 50° C. until no further dissolution is apparent. The cooled (0°) mixture is treated with carbodiimide (R'—N=C=N—R"; 0.011 mol) with continued stirring for two days. The resultant solution or suspension is poured into ice water. The precipitate is filtered off and washed with water. It is purified by being homogenized with and filtered from (a) $CH_2Cl_2$ (2×50 ml); (b) 0.1 N-NaOH (2×50 ml); (c) 0.1N-HCl (2×50 ml); (d) $H_2O$ (2×50 ml); and (e) ether (2×50 ml). The resultant powder is dried.

SCHEME III

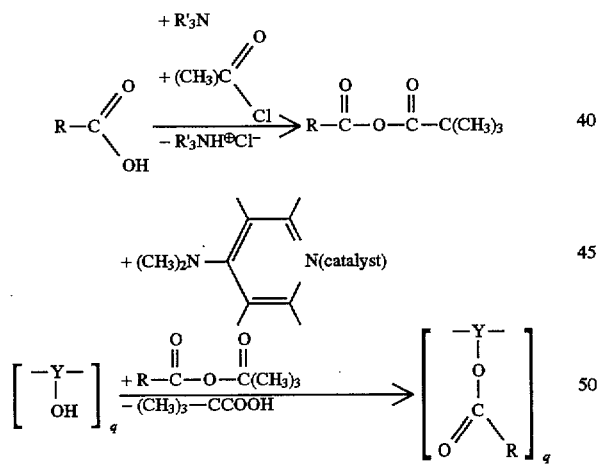

This scheme is suitable for cases were Q is a hydroxyl group-containing polymer that is soluble or swellable in dimethyl formamide. The bulky t-butyl group in pivalic acid prevents acylation by it, and dimethylamino pyridine catalyzes the difficult O-acylation. By-product pivalic acid is removable from the acylated polymer by extraction with organic solvent (e.g. toluene). The scheme is useful for carboxylic acids that are sensitive to the conditions of acylchloride synthesis.

Dry polyvinyl alcohol, methyl cellulose, or a similar swellable carbohydrate ($[Y-OH]_q$; 0.01 mol-OH; where "q" is the number of repeating hydroxy-containing units in the polymeric compound) is rapidly stirred in absolute dimethyl formamide ("DMF," 50 ml) at 50° C. until no further dissolution is apparent. Separately, the carboxylic acid (RCOOH; 0.01 mol) is dissolved in absolute tetrahydrofuran (30 ml). At -10° C., pivaloyl chloride (0.01 mol) is added, followed by drop wise addition of a tertiary amine ($R'_3N$) (0.01 mol, e.g., triethylamine, ethyl diisopropylamine). The precipitated amine hydrochloride is filtered off. The solution is added, drop by drop, to the stirred and cooled (-10° C.) polyol or carbohydrate mixture. The combined mixture is treated at -10° C. with p-dimethyl amino pyridine (0.0001 mol.), and is allowed to come to room temperature and stay there for 15 hours. Toluene (100 ml) is added, with stirring. The mixture is evaporated to dryness in a rotary evaporator. The residue is homogenized in and filtered from (a) toluene (100 ml) and (b) water (2×100 ml). The filtercake is dried in vacuo at 40° C. to constant weight.

SCHEME IV

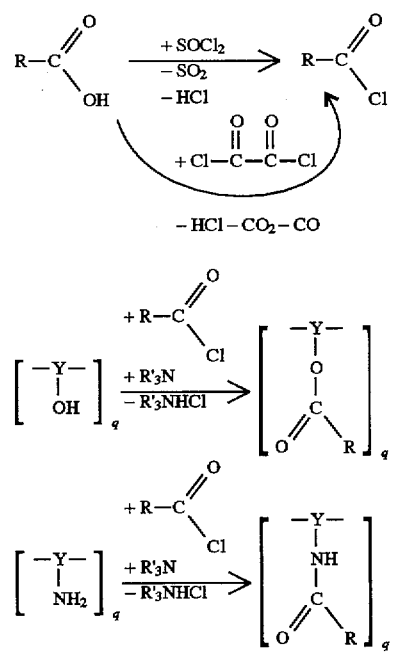

This scheme is useful for cases where Q is a polymer swellable in dimethyl formamide (DMF), and where it needs a highly reactive reagent for acylation. The scheme is suitable for carboxylic acids that form stable acid chlorides.

Carboxylic acid (R—COOH; 0.01 mol) is refluxed with thionylchloride or oxalylchloride (20 ml) until solution is complete and gas evolution ceases. Excess reagent is removed by evaporation. The residual acid chloride is diluted with tetrahydrofuran (10 ml) to give solution A.

A polyamine ($[—Y—NH_2]_q$) such as chitosan, aminoethyl cellulose, polylysine (0.01 mol-$NH_2$), or a polyhydroxy compound ($[—Y—OH]_q$) such as polyvinyl alcohol or a carbohydrate (e.g. methyl cellulose; 0.01 mol-OH) are heated in absolute dimethyl formamide at 50° C., until no further dissolution is apparent. Pyridine (0.01 mol) and p-dimethylaminopyridine (0.01 mol) are added. The mixture is cooled to -10° C., and solution A is added slowly with stirring. After 15 hours at room temperature, toluene (100 mol) is added, and the solution is evaporated in vacuo. The residue is homogenized with and filtered from (a) water (2×100 ml); (b) ether (2×100 ml), and is dried.

SCHEME V

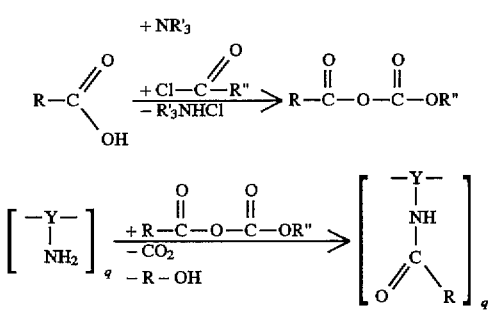

This scheme is useful, where Q is a polyamine swellable or soluble in dimethylformamide. It is especially suitable for cases where the removal of by-products such as salts, acids, or bases) from the final product is difficult, since in this case only carbon dioxide and low molecular weight alcohol are produced as by-products. The scheme is especially useful for carboxylic acids that decompose under the conditions of acid chloride synthesis.

Chitosan, amino ethyl cellulose, polylysine or a similar polyamine ([—Y—$NH_2$]$_q$; 0.01 mol-$NH_2$ groups) is rapidly stirred in dimethyl formamide (30 ml) at 50° C. until no further dissolution is apparent. The carboxylic acid (RCOOH; 0.01 mol) is dissolved in absolute tetrahydrofuran (30 ml). At first trialkylamine (NR'$_3$; 0.01 mol), and then alkylchlorocarbonate (Cl—COOR"; 0.01 mol, where R" is ethyl or isobutyl) is added. The precipitated trialkylammonium chloride (R'$_3$NHCl) is filtered off. The filtrate is added, with stirring, to the cold (−30° C.) polyamine solution. After being stored for 15 hours at −15° C., the mixture is poured on ice (300 g), with stirring. After the ice has melted, the precipitate is filtered off, is thoroughly washed with water, and is dried.

The foregoing may be better understood from the following examples, which are presented for purposes of illustration and are not intended to limit the scope of the invention. As used in the following examples, the references to compounds such as (1), (2), (3) etc., and to substituents such as R, $R_1$, $R_2$ etc., refer to the corresponding compounds and substituents in the foregoing reaction schemes and in formula I.

EXAMPLE 1

Poly-N-[(1-benzoyl-2-methyl-5-methoxy-3-indolyl)-acetyl] chitosan

A) (1-Benzoyl-2-methyl-5-methoxy-3-indolyl)acetic acid

A solution of 15 g. of methyl-(2-methyl-5-methoxy-3-indolyl) acetate and 0.2 g. of sodium in 60 ml. of benzyl alcohol is slowly fractionated over a period of 4½ hours through a Vigreux column to remove methanol. The excess benzyl alcohol is then removed by distillation at 60° C. (2.5 mm.) to give a residue of 18.6 g. of benzyl-(2-methyl-5-methoxy-3-indolyl)-acetate.

B) 10 g. of the benzyl ester obtained above is added to 3.3 g. of 51% sodium hydride-mineral oil emulsion in 260 ml. of dimethylformamide by stirring the mixture for 20 minutes under nitrogen with ice-cooling. To this mixture is added 7.7 ml. of p-chlorobenzoyl chloride dropwise over 30 minutes, and the reaction mixture is stirred in an ice-bath for 5 hours under nitrogen. It is then poured into a mixture of 500 ml. ether, 5 ml. of acetic acid, and one liter of iced water. The organic products are extracted with 3×300 ml. of ether. The ether solutions are combined and washed with a large quantity of water, and dried over sodium sulfate. The solution is filtered, evaporated to near dryness, and the residue charged onto a chromatographic column of 340 g. of alumina and eluting with 20–30% ether in petroleum ether. From these eluates there is obtained benzyl-(1-benzoyl-2-methyl-5-methoxy-3-indolyl)-acetate, M.P. 91°–92° C.

C) 1.5 g. of the ester obtained in part B above is added to 20 ml. of ethyl acetate containing a drop of acetic acid and reduced catalytically at room temperature in the presence of palladium on charcoal catalyst. When the reduction is complete the catalyst is removed by filtration and the filtrate evaporated to a crystalline residue. This residue is recrystallized from aqueous ethanol to give 1-benzoyl-(2-methyl-5-methoxy-3-indolyl)acetic acid, M.P. 172°–173° C. Alternatively, the residue obtained on removal of the reaction solvent may be purified by dissolving in chloroform and precipitating by addition of petroleum ether to the chloroform solution.

D) (1-benzoyl-2-methyl-5-methoxy-3-indolyl) acetic acid (1-benzoyl-2-methyl-5-methoxy-3-indolyl) acetic acid (0.02 mol.) is conjugated to chitosan gel (0.01 mol-$NH_2$) according to Scheme I. The procedure yields the desired compound ($R_1$=2-methyl; $R_2$=N-benzoyl; $R_3$=hydrogen; $R_4$=5-methoxy; $X_n$=(CH)$_4$; n=1; m=1; q>50; p/q>0.9; p>45.)

EXAMPLE 2

Poly-ε-[(1-ρ-chlorobenzoyl-2-methyl-5-methoxy-3-indolyl)-α-propionyl] polylysine A) 1-ρ-Chlorobenzoyl-2-Methyl-5-Indolyl-α-Propionic Acid To a solution 20.0 g. (0.07 mole) of t-butyl-α-(2-methyl-5-methoxy-3-indolyl)-propionate in 270 ml. dimethylformamide is added in small portions 7.0 (0.14 mole) of 51% sodium hydride in mineral oil under $N_2$ with stirring and ice-cooling. After 15 minutes, 17.5 g (0.10 mole) of the ρ-chlorobenzoyl chloride is added dropwise, a white precipitate separates out almost immediately. The mixture is stirred at 0° for 2 hours and is allowed to stand in the cold room overnight. The next morning, the mixture is filtered and diluted with ether. One-half of the solution is washed with water, sodium bicarbonate, water successively and dried over sodium sulfate. The dried solution is concentrated to a syrup which is chromatographed on 400 g. of acid-washed alumina. After mineral oil and trace of impurity is eluted by petroleum ether and 5% ether in petroleum ether, the desired product is obtained by elution with 10% ether in petroleum ether as yellow oil. The other half is similarly treated.

B) The above ester and a few pieces of porous plate chips are placed in a flask submerged in an oil bath. A steady stream of $N_2$ is introduced into the flask through the opening while the temperature of the oil bath is slowly raised to 215°. After ½ hour at 215°, the mixture is dissolved in ether, filtered and washed with sodium bicarbonate. The bicarbonate extract is acidified with dilute hydrochloric acid, and the precipitate is taken into ether, washed with water, dried over sodium sulfate and evaporated to dryness. The solid residue is recrystallized from a mixture of benzene and petroleum ether to give the desired acid, M.P. 87°–88°.

C) Poly-ε-[(1-ρ-chlorobenzoyl-2-methyl-5-methoxy-3-indolyl)-α-propionyl] polylysine 1-p-chlorobenzoyl-2-methyl-5-methoxy-3-indolyl-α-propionic acid (0.01 mol.) is conjugated to polylysine (0.01 mol-$NH_2$) according to Scheme II. The procedure yields the desired compound ($R_1$=2-methyl; $R_2$=N-p-chlorobenzoyl; $R_3$=$CH_3$; $R_4$=5-methoxy; $X_n$=$(CH)_4$; n=1; m=2; Q=polylysine; q>50; p/q>0.9; p>45.)

EXAMPLE 3

Poly-N-[(1-Benzoyl-4-Trifluoromethyl-3-Indolyl)-Acetyl] Chitosan

A) 1-Benzoyl-4-Trifluoromethyl-3-Indolyl Acetic Acid (1) A solution of 0.05 mole of methyl-(4-trifluoromethyl-3-indolyl) acetate and 0.01 mole of sodium in 60 ml. anhydrous benzyl alcohol is slowly fractioned over a period of 4½ hours through a Vigreux column to remove methanol. The excess benzyl alcohol is removed by distillation at 60° and 2.5 mm. to give a residue of crude benzyl-(4-trifluoromethyl-3-indolyl) acetate.

(2) A suspension of 0.046 mole of 50% sodium hydride-mineral oil in 250 ml. of dimethylformamide is stirred for 20 minutes under nitrogen, with ice-cooling. Then 0.035 mole of the benzyl ester obtained above is added, and the mixture is stirred for 20 minutes. 0.046 mole of p-benzoylchloride in 50 ml. of dimethylformamide is added dropwise over a period of 30 minutes. The mixture is stirred in an ice-bath for 5 hours under nitrogen, then poured into a mixture of 500 ml. of ether, 5 ml. of acetic acid and 1.1 of iced water. The organic products are extracted with 3×300 ml. of ether. The ether solutions are combined and washed with a large quantity of water, and dried over sodium sulfate. The solution is filtered, evaporated to near dryness and the residue charged onto a 300 g. alumina column. The crude benzyl-(1-benzoyl-4-trifluoromethyl-3-indolyl) acetate is eluted with ether-petroleum ether (5–50% v./v.).

(3) 0.02 mole of the ester combined in part (A)(2) is added to 50 ml. of ethyl acetate containing a drop of acetic acid and is reduced catalytically at room temperature in the presence of palladium on charcoal catalyst. Upon completion of the reduction, the catalyst is removed by filtration and the filtrate evaporated to yield 1-benzoyl-4-trifluoromethyl-3-indolyl acetic acid.

(B) Poly-N-[(1-benzoyl-4-trifluoromethyl-3-indolyl) acetyl] chitosan 1-benzoyl-4-trifluoromethyl-3-indolyl acetic acid (0.01 mol.) is conjugated to chitosan (0.01 mol-$NH_2$) according to Scheme II. The procedure yields the desired compound ($R_1$=hydrogen; $R_2$=N-benzoyl; $R_3$=hydrogen; $X_n$=$(CH)_4$; n=1; m=1; $R_4$=4-trifluoromethyl; Q=chitosan; q>50; p/q>0.9; p>45.)

EXAMPLE 4

Poly-ε-[(1-benzoyl-5-dimethylamino-4-trifluoromethyl-3-indolyl) acetyl]-polylysine A) (1-Benzoyl-5-Dimethylamino-4-Trifluoromethyl-3-indolyl) Acetic Acid A mixture of 10 cc. of glacial acetic acid and 5.0 ml. of a 37% aqueous solution of formaldehyde is added to a solution of 0.01 mole of (1-benzoyl-4-trifluoromethyl-5-nitro-3-indolyl) acetic acid in 150 ml. of distilled dimethoxyethane. This mixture is reduced with Raney nickel at 40 p.s.i. and room temperature. After the theoretical amount of hydrogen has been taken up, the reaction mixture is filtered. The catalyst is washed well with ether. The combined filtrate and ether washings are washed with water, dried over sodium sulfate and evaporated in vacuo to yield (1-benzoyl-5-dimethylamino-4-trifluoromethyl-3-indolyl) acetic acid.

B) Poly-ε-[(1-benzoyl-5-dimethylamino-4-trifluoromethyl-3-indolyl) acetyl] polylysine (1-benzoyl-5-dimethylamino-4-trifluoromethyl-3-indolyl) acetic acid (0.01 mol.) is conjugated to polylysine (0.01 mol-$NH_2$) according to Scheme II. The procedure yields the desired compound ($R_1$=hydrogen; $R_2$=N-benzoyl; $R_3$=hydrogen; $R_4$=5-dimethylamino and 4-trifluoromethyl; $X_n$=$(CH)_4$; n=1; m=1; Q=polylysine; q>50; p/q>0.9; p>45.)

EXAMPLE 5

Poly-N-[(1-Benzoyl-5-hydroxy-4-trifluoromethyl-3-indolyl)-acetyl] chitosan

A) (1-Benzoyl-5-Hydroxy-4-Trifluoromethyl-3-Indolyl) Acetic Acid 0.001 mole of 1-benzoyl-5-methoxy-4-trifluoromethyl-3-indolyl acetic acid is added portionwise, with stirring, to 1.5 g. of pyridine hydrochloride at 160°–220°. On cooling, the residue is extracted with saturated sodium bicarbonate solution and made neutral with 1.0N HCl. The solution is then extracted with ether, and the ether extracts washed well with water and dried over sodium sulfate. The ether solution is concentrated to give 1-benzoyl-5-hydroxy-4-trifluoromethyl-3-indolyl acetic acid.

B) Poly-N-[(1-Benzoyl-5-hydroxy-4-trifluoromethyl-3-indolyl)acetyl] chitosan (1-Benzoyl-5-hydroxy-4-trifluoromethyl-3-indolyl) acetic acid (0.02 mol.) is conjugated to chitosan gel (0.01 mol-$NH_2$) according to Scheme I. The procedure yields the desired compound ($R_1$=hydrogen; $R_2$=N-benzoyl; $R_3$=hydrogen; $R_4$=5-hydroxy and 4-trifluoromethyl; $X_n$=$(CH)_4$; n=1; Q=chitosan; m=1; q >50; p/q>0.9; p>45.)

EXAMPLE 6

N-Indomethacinyl-chitosan

Indomethacin (0.02 mol.) is conjugated to chitosan gel (0.01 mol-$NH_2$) according to Scheme I. The procedure yields the desired compound ($R_1$=2—$CH_3$; $R_2$=N-p-chlorobenzoyl; $R_3$=hydrogen; $R_4$=5—$CH_3O$; $R_5$=hydrogen; $X_n$=$(CH)_4$; n=1; m=1; Q=chitosan; q>50; p/q>0.9; p>45.)

EXAMPLE 7

Poly-ε-[(1-Benzoyl-4-Fluoro-3-indolyl) acetyl] polylysine

A) (1-Benzoyl-4-Fluoro-3-Indolyl)-Acetic Acid (1) A solution of 0.05 of a mole of methyl-(4-fluoro-3-indolyl)-acetate and 0.01 of a mole of sodium in 60 ml. of benzyl alcohol is slowly fractionated over a period of 4½ hours through a Vigreux column to remove methanol. The excess benzyl alcohol is then removed by distillation at 60° C. (2.5 mm.) to give a residue of benzyl-(4-fluoro-3-indolyl)-acetate.

(2) A suspension of 0.046 m. of 50% sodium hydride-mineral oil in 250 ml. of dimethylformamide is stirred for 20 minutes under nitrogen with ice-cooling. Then 0.035 m. of the benzyl ester obtained above is added and the mixture stirred for 20 minutes. To the above mixture, 0.046 m. of benzoyl chloride in 50 ml. of dimethylformamide is added dropwise over a period of 30 minutes. The mixture is stirred in an ice-bath for 5 hours under nitrogen. It is then poured into a mixture of 500 ml. of ether, 5 ml. of acetic acid and 1 l of iced water. The organic products are extracted with 3×300 ml. of ether. The ether solutions are combined and washed with a large quantity of water, and dried over sodium sulfate. The residue charged onto a 300 g. alumina column. The crude benzyl-(1-benzoyl-4-fluoro-3-indolyl)-acetate is eluted with ether-petroleum ether (5–50% v./v.).

(3) 0.02 of a mole of the ester obtained in part (A)(2) is added to 50 ml. of ethyl acetate containing a drop of acetic acid and is reduced catalytically at room temperature in the presence of palladium on charcoal catalyst. Upon completion of the reduction, the catalyst is removed by filtration and the filtrate evaporated to yield (1-benzoyl-4-fluoro-3-indolyl)-acetic acid.

B) Poly-ε-[(1-Benzoyl-4-Fluoro-3-indolyl)acetyl] polylysine (1-Benzoyl-4-fluoro-3-indolyl)-acetic acid (0.01 mol.) is conjugated to polylysine (0.01 mol-$NH_2$) according to Scheme II. The procedure yields the desired compound ($R_1$=hydrogen; $R_2$=N-benzoyl; $R_3$=hydrogen; $R_4$=4-fluoro; $X_n$=$(CH)_4$; n=1; m=1; Q=polylysine; q>50; p/q>0.9; p>45.)

EXAMPLE 8

Poly-N-[(1-Chlorobenzoyl-7-Methoxy-3-Indolyl)-Acetyl] Chitosan

A) (6-methoxy-3-indolyl)-acetic anhydride 0.049 mole of dicyclohexylcarbodiimide is dissolved in a solution of 0.10 mole of 6-methoxy-3-indolyl acetic acid in 200 ml. tetrahydrofuran and allowed to stand at room temperature for 2 hours. The precipitated urea is removed by filtration, and the filtrate is evaporated in vacuo to a residue and flushed with Skellysolve B. The residual oily anhydride obtained is used without purification in the next step.

B) (1-Butyl-6-methoxy-3-indolyl)-acetate 25 mls. of t-butyl alcohol and 0.3 gm. of fused zinc chloride are added to the anhydride from part A. The solution is refluxed for 16 hours, and the excess alcohol is removed in vacuo. The residue is then dissolved in ether and washed several times with saturated salt solution. The ether extract is dried over magnesium sulfate, and the solution treated with charcoal. The ether solution is then evaporated and flushed several times with Skellysolve B for complete removal of the alcohol. This residual oil ester is used without purification in the next step.

C) (t-butyl-1-ρ-chlorobenzoyl-6-methoxy-3-indolyl)-acetate 0.065 mole of the crude ester, as obtained in step B, is added to 450 mls. of dimethylformamide and cooled to 4° in an ice bath. 0.098 mole of a 50% suspension of sodium hydride is added portionwise to this stirred solution. After 15 minutes, 0.085 mole of ρ-chlorobenzoyl chloride is added over a 10 minute interval. This mixture is then stirred for 9 hours, without replenishing the ice bath. At this time, the mixture is poured into 1 liter of 5% acetic acid, extracted with a mixture of ether and benzene and washed thoroughly with water, sodium bicarbonate solution and a saturated salt solution. The ether extract is dried over magnesium sulfate, treated with charcoal and evaporated to a residue. The crude product, thus obtained, is chromatographed on 600 gms. of acid-washed alumina using a mixture of (v./v. 5–50%) ether-petroleum ether as eluent.

D) (1-ρ-chlorobenzoyl-6-methoxy-3-indolyl) acetic acid

A mixture of 1.0 g. of the ester obtained in step C and 0.1 powdered porous plate is heated, with stirring, in an oil bath at 210° C. under nitrogen, then dissolved in benzene and ether, filtered and extracted with sodium bicarbonate solution. The aqueous solution is filtered by suction to remove ether, neutralized with acetic acid, then acidified weakly with dilute hydrochloric acid. The crude product is then recrystallized from aqueous ethanol and dried in vacuo.

E) Poly-N-[(1-Chlorobenzoyl-7-Methoxy-3-Indolyl) Acetyl] Chitosan

1-ρ-chlorobenzoyl-6-methoxy-3-indolyl acetic acid (0.01 mol.) is conjugated to chitosan (0.01 mol-$NH_2$) according to Scheme II. The procedure yields the desired compound ($R_1$=hydrogen; $R_2$=N-ρ-chlorobenzoyl; $R_3$=hydrogen; $R_4$=6-methoxy; $X_n$=$(CH)_4$; n=1; m=1; Q=chitosan; q>50; p>0.9; p>45.)

EXAMPLE 9

Poly-N-[(1-ρ-Chlorobenzoyl-5,7-Dimethoxy-3-Indolyl) Acetyl] Chitosan (I) 1-ρ-Chlorobenzoyl-5,7-Dimethoxy-3-Indolyl Acetic Acid A) 5,7-dimethoxygramine A solution of 0.032 mole of 5,7-dimethoxyindole in 40 mls. of dioxane is added dropwise, over a period of 30 minutes, to an ice-cooled, stirred mixture of 40 mls. of dioxane, 40 mls. of acetic acid, 3.2 mls. of 36% aqueous formaldehyde and 8.8 mls. of 25% aqueous dimethylamine. The clear solution is stirred and cooled for two hours and then allowed to warm up to room temperature over night. To this solution is added 500 mls. of water. The turbid mixture is then treated with charcoal and filtered through a siliceous filter aid. The clear filtrate is made alkaline with 400 mls. of dilute sodium hydroxide solution, and placed in a refrigerator, to cool. This mixture is then filtered, and the solid gramine is washed with water and dried.

B) 5,7-dimethoxy-indolyl-3-acetonitrile 0.106 mole of the gramine obtained in A is added to 420 mls. of methyl iodide, with vigorous stirring, over a period of 20 minutes. The reaction mixture is then allowed to remain at 5° for 15 hours. The solution is filtered, and the iodine metholate cake is dried at 50°. This solid is dissolved in a solution of 60 gms. of sodium cyanide in 1 liter of water and warmed for 2 hours at 80°. The desired product is extracted with chloroform which is then evaporated to give a crude oily product. The oil is then dissolved in 250 mls. of ether, filtered, and the filtrate concentrated. This concentrate is then diluted with petroleum ether, at which point the 5,7-dimethoxy-indolyl-3-acetonitrile precipitates. The mixture is then filtered and the cake dried.

C) 5,7-dimethoxy-indolyl-3-acetic acid 0.08 mole of the nitrile obtained from B is added to a solution of 140 mls. of alcohol, 100 ml. of water and 4.3 gms. of potassium hydroxide and refluxed for 15 hours. The mixture is brought to room temperature, and 60 mls. of glacial acetic acid is added. The solution is then filtered through a talc filter, and the filtrate diluted with 500 mls. of water. The precipitated 5,7-dimethoxy-indolyl-3-acetic acid is then filtered and dried.

D) 1-ρ-chlorobenzoyl-5,7-dimethoxy-3-indolyl acetic acid

The procedure of Example 8A, 8B and 8D is followed using the product of part C of this example in place of the 6-methoxy-3-indolyl acetic acid, to produce 1-ρ-chlorobenzoyl-5,7-dimethoxy-3-indolyl acetic acid. When 5,6-dimethoxy-3-indolyl acetic acid is used in place of 6-methoxy-3-indolyl acetic acid in the above procedure, there is obtained 1-ρ-chlorobenzoyl-5,6-dimethoxy-3-indolyl acetic acid.

When 5,6-methylenedioxyindole or 2-methyl-6-methoxyindole is used in place of 5,7-dimethoxyindole in the procedure of Parts A, B and C, there is obtained 5,6-methylenedioxy-3-indolyl acetic acid, which where used in the procedure of Part D gives 1-ρ-chlorobenzoyl-5,6-methylenedioxy-3-indolyl acetic acid of 1-ρ-chlorobenzoyl-2-methyl-6-methoxy-3-indolyl acetic acid.

(II) Poly-N-[(1-ρ-Chlorobenzoyl-5,7-Dimethoxy-3-Indolyl) Acetyl] Chitosan

1-ρ-chlorobenzoyl-5,7-dimethoxy-3-indolyl acetic acid (0.01 mol.) is conjugated to polylysine (0.01 mol-$NH_2$) according to Scheme II. The procedure yields poly(1-ρ-chlorobenzoyl-5,7-dimethoxy-3-indolyl)N-acetyl-chitosan ($R_1$=hydrogen; $R_2$=hydrogen; $R_3$=hydrogen; $R_4$=5,7 dimethoxy; $X_n$=$(CH)_4$; n=1; m=1; Q=polylysine; q>50; p/q>0.9; p>45.)

(III) When 1-ρ-chlorobenzoyl-5,6-dimethoxy-3-indolyl acetic acid used in part II, the product obtained is poly(1-ρ-chlorobenzoyl-5,6-dimethoxy indolyl)N-acetyl chitosan. When 1-ρ-chlorobenzoyl-5,6-methylenedioxy-3-indolyl acetic acid or 1-ρ-chlorobenzoyl-2-methyl-6-methoxy-3-indolyl acetic acid is used in part II, the corresponding polyindolyl-N-acetyl chitosans are obtained.

EXAMPLE 10

Poly-N-[(1-ρ-Chlorobenzoyl-4-Methoxy-3-Indolyl) Acetyl] Chitosan (I) 1-ρ-Chlorobenzoyl-4-Methoxy-3-Indolyl Acetic Acid
A) Methyl 4-hydroxy-3-Indolyl acetate A solution of methyl 4-benzyloxy-3-indolyl acetate (4.0 g.) in 150 ml. methanol is shaken with 3 g. palladium on charcoal and hydrogen until the hydrogen uptake ceases. The catalyst is filtered and the filtrate is taken to dryness in vacuo.

B) Methyl 4-methoxy-3-indolyl acetate

A solution of methyl 4-hydroxy-3-indolyl acetate (10.5 gms., 0.065 m.) in 96 ml. 10% sodium hydroxide is stirred and treated with 7.5 ml. dimethyl sulfate. After stirring for several hours, the crude product is extracted with ether, washed with water and dried over sodium sulfate. The ether solution is evaporated in vacuo and the residue is chromatographed on 200 g. of acid-washed alumina using a mixture of ether-petroleum ether (v./v. 25–50%) as the eluent.

C) 4-methoxy-3-indolyl acetic acid

A solution of methyl 4-methoxy-3-indolyl acetate in excess 2N absolute ethanolic potassium hydroxide is allowed to stand overnight, diluted with water and extracted with ether. The aqueous layer is acidified. The precipitate is collected and recrystallized from aqueous ethanol.

D) Poly-N-[(1-ρ-chlorobenzoyl-4-methoxy-3-indolyl) acetyl] chitosan

The procedure of Examples 8A, 8B, 8C and 8D is followed using the product of part C in place of 6-methoxy-3-indolyl acetic acid, to produce 1-ρ-chlorobenzoyl-4-methoxy-3-indolyl acetic acid.

(II) Poly-N-[(1-ρ-chlorobenzoyl-4-methoxy-3-indolyl) acetyl] chitosan

1-ρ-chlorobenzoyl-4-methoxy-3-indolyl acetic acid (0.02 mol.) is conjugated to chitosan gel (0.01 mol-$NH_2$) according to Scheme I. The procedure yields the desired compound ($R_1$=hydrogen; $R_2$=N-ρ-chlorobenzoyl; $R_3$=hydrogen; $R_4$=4-methoxy; $X_n$=$(CH)_4$; n=1; m=1; Q =chitosan; q>50; p/q>0.9; p>45.)

EXAMPLE 11

Poly-N-[(1-ρ-Chlorobenzoyl 5-Chloro-6-Methoxy-3-Indolyl) Acetyl] Chitosan (I) 1-ρ-Chlorobenzoyl-5-chloro-6-methoxy-3-indolyl acetic acid A) 5-chloro-6-methoxy-3-indolyl acetic acid When 5-chloro-6-methoxy-3-indolylacetonitrile is used in place of 5,7-dimethoxy-indolyl-3-acetonitrile in the procedure of Example 9C, there is obtained 5-chloro-6-methoxy-3-indolyl acetic acid.

B) 1-ρ-chlorobenzoyl-5-chloro-6-methoxy-3-indolyl acetic acid

When the procedures of Examples 8A–8D are followed using 5-chloro-6-methoxy-3-indolyl acetic acid as the starting material, there is obtained 1-ρ-chlorobenzoyl-5-chloro-6-methoxy-3-indolyl acetic acid.

C) 1-ρ-chlorobenzoyl-2-methyl-7-methoxy-3-indolyl acetic acid

When 2-methyl-7-methoxyindole is used in place of 5,7 dimethoxyindole in the procedures of Examples 9A–9D and the product is used in the procedures of Examples 8A–8D, there is obtained 1-ρ-chlorobenzoyl-2-methyl-7-methoxy-3-indolyl acetic acid.

(II) Poly-N-[(1-ρ-Chlorobenzoyl 5-Chloro-6-Methoxy-3-Indolyl) Acetyl] Chitosan

1-ρ-chlorobenzoyl-5-chloro-6-methoxy-3-indolyl acetic acid (0.02 mol.) is conjugated to chitosan gel (0.01 mol-$NH_2$) according to Scheme I. The procedure yields the desired compound ($R_1$=hydrogen; $R_2$=N-ρ-chlorobenzoyl; $R_3$=hydrogen; $R_4$=6-methoxy; $X_n$=$(CH)_4$; n =1; m=1; Q=chitosan; q>50; p/q>0.9; p>45.)

When 1-p-chlorobenzoyl-2-methyl-7-methoxy-3-indolyl acetic acid is used in the procedure of Part II, the corresponding indolyl-N-acetyl-chitosan is obtained.

EXAMPLE 12

Poly-ε-[(1-ρ-Chlorobenzoyl-2-Methyl-4-Methoxy-3-Indolyl) Acetyl] Polylysine (I) 1-ρ-chlorobenzoyl-2-methyl-4-methoxy-3-indolyl acetic acid
A) 2-methyl-4-methoxyindole.

(1) 6-methoxy-2-nitrobenzoyl chloride is produced by adding 0.046 mole of 6-methoxy-2-nitrobenzoic acid to 60 mls. of redistilled thionyl chloride and refluxing the mixture for 2 hours. The excess reagent is removed under reduced pressure, maintaining the temperature below 40°. The residue is washed with benzene and then removed under reduced pressure. This residue is placed over sodium hydroxide, in vacuo overnight.

(2) Diazomethyl-6-methoxy-2-nitrophenylketone.

A solution of 0.044 mole of the 6-methoxy-2-nitrobenzoyl chloride obtained from (1) in 30 mls. of dioxane is added to a solution of 50 mls. of diazomethane in 200 ml. of ether, with agitation at 0°. The reaction mixture is allowed to remain overnight at room temperature. The solvent is then removed under reduced pressure to yield a residue contained the ketone. The 6-methoxy-2-nitrophenyl diazomethyl ketone is crystallized from this residue using dioxane.

(3) 6-methoxy-2-nitrophenylacetic acid.

A solution of 0.044 mole of the diazoketone obtained in (2) in 75 mls. of dioxane, is added over a period of 20 minutes to a freshly prepared solution of 4.0 gms. of silver oxide, 3.0 gms. of sodium thiosulfate and 5.0 gms. of sodium carbonate in 150 mls. of distilled water. The temperature of the reaction mixture is maintained at 50°–60° during the addition and for an additional hour. At this point, the mixture is brought to a temperature of 90°–95° for ½ hour. The mixture is then filtered, and the filtrate is diluted with 200 mls. of water, acidified with dilute nitric acid and extracted with chloroform (3×200 mls.) The combined chloroform extract is washed with 50 mls. of water and dried over sodium sulfate. The chloroform is then removed, and the residue extracted with boiling water (2×100 mls.). Concentration of the water solution, followed by cooling, precipitates the 6-methoxy-2-nitrophenyl acetic acid.

(4) Ethyl-6-methoxy-2-nitrophenylacetyl malonate.
The product from A(3) is used in the procedure of part A(1) to give the corresponding acid chloride. A solution (0.02 mole) of this compound in 25 ml. of ether is gradually added to a refluxing ether solution of ethyl ethoxymagnesiomalonate. Heating is continued until stirring is difficult due to formation of a viscous oil. The cooled mixture is then shaken with dilute $H_2SO_4$ (2.5 g. in 20 ml. H20) until the oily magnesium complex has dissolved. The ethereal phase is separated, washed with water, and dried over $Na_2SO_4$. Evaporation yields the crude ethyl-6-methoxy-2-nitrophenylacetylmalonate.

(5) 6-methoxy-2-nitrophenylacetone.
A solution of 5.7 gms. of the product from A(4), 12 mls. of acetic acid, 1.5 mls. of sulfuric acid and 8 mls. of water is refluxed for 6 hours. The cooled solution is made alkaline with 5N sodium hydroxide and extracted with ether (3×50 mls.). The combined etheral extract is washed with water, dried over sodium sulfate, and evaporated to give an oil which rapidly solidifies. Crystallization of this solid from ethanol yields 6-methoxy-2-nitrophenylacetone.

(6) 4-methoxy-2-methylindole—1.2 gms. of the product from A(5) is added to a mixture of 100 mls. of ethyl alcohol and 1.0 gm. of Raney nickel. This solution is shaken at room temperature and atmospheric pressure, in hydrogen for ½ hour. The solution is then filtered, and the filtrate evaporated under reduced pressure. Crystallization from light petroleum ether yields 4-methoxy-2-methylindole.

B) 2-methyl-4-methoxy-3-indolyl acetic acid

When 4-methoxy-2-methylindole is used in place of 5,7-dimethoxyindole as described in Examples 9A–9C, there is obtained 2-methyl-4-methoxy-3-indolyl acetic acid.

C) 1-ρ-chlorobenzoyl-2-methyl-4-methoxy-3-indolyl acetic acid

When the product from 12(I)(B) is used in place of 6-methoxy-3-indolyl acetic acid as described in Examples 8A–8D, there is obtained 1-ρ-chlorobenzoyl-2-methyl-4-methoxy-3-indolyl acetic acid.

(II) Poly-ε-[(1-ρ-Chlorobenzoyl-2-Methyl-4-Methoxy-3-Indolyl) Acetyl] Polylysine 1-ρ-chlorobenzoyl-2-methyl-4-methoxy-3-indolyl acetic acid 1-ρ-chlorobenzoyl-2-methyl-4-methoxy-3-indolyl acetic acid (0.01 mol.) is conjugated to polylysine (0.01 mol-$NH_2$) according to Scheme II. The procedure yields the desired compound ($R_1=CH_3$; $R_2=N$-ρ-chlorobenzoyl; $R_3$=hydrogen; $R_4$=4-methoxy; Q=polylysine; n=1; m=1; q>50; p/q>0.9; p>45.)

EXAMPLE 13

Poly-N-[(1-ρ-Chlorobenzoyl-7-Methoxy-5-Methyl-3-Indolyl) Acetyl] Chitosan

I) 1-ρ-Chlorobenzoyl-7-Methoxy-7-Methoxy-5-Methyl-3-Indolyl Acetic Acid
A) 7-methoxy-5-methylindole 0.1 mole of 4-methyl-o-anisidine is added to 0.1 mole of monochloroacetaldehyde and the mixture refluxed for 2 hours. The water formed is distilled off and the residue is heated at 210°–220° for an additional hour. This residue is then chromatographed on acid-washed alumina and eluted with ether, petroleum-ether. The eluent is removed under reduced pressure and 7-methoxy-5-methylindole is obtained.

B) 1-ρ-chlorobenzoyl-7-methoxy-5-methyl-3-indolyl acetic acid

The product from part A is used in the procedures of Examples 8A–8D. There is obtained 1-ρ-chlorobenzoyl-7-methoxy-5-methyl-3-indolyl acetic acid.

C) 1-ρ-chlorobenzoyl-5-fluoro-7-methoxy-3-indolyl acetic acid

The procedures of parts A and B are followed, starting with 4-fluoro-o-anisidine, to give 1-ρ-chlorobenzoyl-5-fluoro-7-methoxy-3-indolyl acetic acid.

D) 1-ρ-chlorobenzoyl-5-nitro-7-methoxy-3-indolyl acetic acid

The procedure of parts A and B are followed staring with 4-nitro-o-anisidine, to give 1-ρ-chlorobenzoyl-5-nitro-7-methoxy-3-indolyl acetic acid.

(II) Poly-N-[(1-ρ-Chlorobenzoyl-7-Methoxy-5-Methyl-3-Indolyl) Acetyl] Chitosan

1-ρ-chlorobenzoyl-7-methoxy-5-methyl-3-indolyl acetic acid (0.02 mol.) is conjugated to chitosan gel (0.01 mol-$NH_2$) according to Scheme I. The procedure yields the desired compound ($R_1$=hydrogen; $R_2$=N-ρ-chlorobenzoyl; $R_3$=hydrogen; $R_4$=7-methoxy and 5-methyl; $X_n$=$(CH)_4$; n=1; m=1; Q=chitosan; q>50; p/q>0.9; p>45.)

EXAMPLE 14

Poly-ε-[(1-ρ-Chlorobenzoyl-2-Allyl-5-Methoxy-3-Indolyl) Acetyl] Polylysine (I) 1-p-Chlorobenzoyl-2-Allyl-5-Methoxy-3-Indolyl Acetic Acid
A) 5-methoxy-2-indolyl acetaldehyde A solution of 5-methoxy-2-indolylacetyl chloride (0.1 mol.) in dry tetrahydrofuran is treated with 0.25 mole of lithium aluminum tri-t-butoxy hydride with ice-cooling and stirring. After the initial reaction, the mixture is stirred at room temperature for 4 hours and poured into ice. Excess of acetic acid is added, and the product is extracted with ether. The ethereal solution is washed with sodium bicarbonate, dried over sodium sulfate, and evaporated to a syrup. Chromatography of the residue on a column of silica gel, using ether-petroleum ether (v./v.) 10–30% as eluent, gives 5-methoxy-2-indolyl acetaldehyde.

B) 2-allyl-5-methoxy indole

A solution of 0.1 mole of the aldehyde and 0.12 mole of methylene triphenylphosphine, prepared in situ from 0.12 mole of methyl triphenylphosphonium iodide and 0.12 mole of n-butyl lithium, in benzene is stirred at room temperature for 4 hours and then at 80° for 1 hour. The solution is washed with 0.5N hydrochloric acid, water and dried over sodium sulfate. Evaporation of the solvent in vacuo and chromatography of the residue on a column of 300 g. acid-washed alumina, using ether-petroleum ether (v./v.) 0–20% as eluent, gives 2-allyl-5-methoxy indole.

C) 2-allyl-5-methoxygramine

A solution of 0.032 mole of 2-allyl-5-methoxy indole in 40 ml. of dioxane is added dropwise, over 30 minutes, to an ice-cooled, stirred mixture of 40 ml. dioxane, 40 ml. acetic acid, 3.2 ml. 36% aqueous formaldehyde and 8.8 ml. 25% aqueous dimethylamine. The clear solution is stirred and cooled for two hours and then allowed to warm to room temperature overnight. To this solution is added 500 ml. of water. The turbid mixture is then treated with charcoal and filtered through a silicaceons filter acid. The clear filtrate is made alkaline with 400 ml. of dilute NaOH solution and cooled in a refrigerator. The mixture is filtered, and the solid gramine is washed with water and dried.

D) 2-allyl-5-methoxy-3-indolyl acetonitrile 0.106 mole of the gramine from part C is added to 420 ml. of methyl iodide, with vigorous stirring, over a period of 20 minutes. The reaction mixture is then allowed to remain at 5° for 15 hours. The solution is filtered, and the iodine metholate cake is dried at 50° C. The solid is dissolved in a solution of 60 g. NaCN in 1 liter and warmed for 2 hours at 80°. The desired product is extracted with chloroform which is then evaporated to give a crude oily product. The oil is then dissolved in 250 ml. of ether, filtered and the filtrate is concentrated. The concentrate is diluted with petroleum ether, at which point the 2-allyl-5-methoxy-3-indolyl acetonitrile precipitates. The mixture is filtered and the cake dried.

E) 2-allyl-5-methoxy-3-indolyl acetic acid 0.08 mole of 2-allyl-5-methoxy-3-indolyl acetonitrile is added to a mixture of 140 ml. of alcohol, 100 ml. of water and 4.3 g. of KOH. The mixture is refluxed 15 hours and then brought to room temperature. Glacial acetic acid (60 ml.) is added, and the solution is filtered through a talc filter. The filtrate is diluted with 500 ml. of water, and the precipitated 2-allyl-5-methoxy-3-indolyl acetic acid is separated by filtration and dried.

F) 1-p-chlorobenzoyl-2-allyl-5-methoxy-3-indolyl acetic acid

The procedure of Examples 8A–8D is followed using the product of part E in place of the 6-methoxy-3-indolyl acetic acid, to produce 1-p-chlorobenzoyl-2-allyl-5-methoxy-3-indolyl acetic acid.

II) Poly-ε-[(1-p-Chlorobenzoyl-2-Allyl-5-Methoxy-3-Indolyl) Acetyl] Polylysine 1-p-chlorobenzoyl-2-allyl-5-methoxy-3-indolylacetic acid (0.01 mol.) is conjugated to polylysine (0.01 mol-NH$_2$) according to Scheme II. The procedure yields the desired compound ($R_1$=2-allyl; $R_2$=N-p-chlorobenzoyl; $R_3$=hydrogen; $R_4$=5-methoxy; $X_n$=(CH)$_4$; n=1; m=1; Q=polylysine; q>50; p/q>0.9; p>45.)

EXAMPLE 15

Poly-N-Cinmetacinyl Chitosan

Cinmetacin (0.01 mol.) is conjugated to chitosan (0.01 mol-NH$_2$) according to Scheme II. The procedure yields the desired compound ($R_1$=CH$_3$; $R_2$=N-cinnamoyl; $R_3$=hydrogen; $R_4$=5-CH$_3$O; Q=chitosan; $X_n$=(CH)$_4$; n=1; m=1; q>50, p/q>0.9; p>45.

EXAMPLE 16

Polytolmetinyl Polylysine

Tolmetin (0.01 mol.) is conjugated to polylysine (0.01 mol-NH$_2$) according to Scheme V. Specifically, isobutyl chlorocarbonate is used with triethyl amine the tertiary amine. The procedure yields the desired compound ($R_1$=p-toluoyl; $R_2$=N—CH$_3$; $R_3$=hydrogen; Q=polylysine; n=0; m=1; q>40; p/q>0.8; p>32.)

EXAMPLE 17

Polyclopiracyl-methylcellulose

Clopirac (0.01 mol.) is conjugated to methylcellulose (0.01 mol-OH) according to Scheme III. Specifically, triethyl amine is used as the base. The procedure yields the desired compound ($R_1$=CH$_3$; $R_2$=N-p-chlorophenyl; $R_3$=hydrogen; $R_5$=CH$_3$; n=0; m=1; Q=methyl-cellulose; q>100; p/q>0.8; p>80.)

EXAMPLE 18

Polyclometacinyl chitosan

Clometacin (0.02 mol.) is conjugated to chitosan gel (0.01 mol-NH$_2$) according to Scheme I. The procedure yields the desired compound ($R_1$=p-chlorobenzoyl; $R_2$=methyl; $R_3$=hydrogen; $R_4$=6-methoxy; $X_n$=(CH)$_4$; n=1; m=1; Q=chitosan; q>50; p/q>0.9; p>45.)

EXAMPLE 19

Poly-N-[5-(p-Chlorobenzoyl) 1,4 Dimethyl Pyrrole-2-Acetyl] Chitosan

A) Ethyl 1,4-dimethyl-3-ethoxycarbonylpyrrole -2-acetate

To a solution of 500 ml. of 25% aqueous methylamine is added 93 g. (0.46 mole) of diethyl acetone-dicarboxylate. To the mixture is added 72 g. (0.782 mole) of chloroacetone over a 10 min. period. The temperature is kept below 60° C. by external cooling. After two hours, the mixture is poured into ice-hydrochloric acid. The solid is collected by filtration, washed with water and air dried. It is recrystallized from hexane to give ethyl 1,4-dimethyl-3-ethoxycarbonylpyrrole-2-acetate as a white solid, M.P. 71°–72° C.

Analysis-Calcd. for $C_{12}H_{19}NO_4$ (percent): C, 61.64; H, 7.56; N, 5.53. Found (percent): C, 61.64; H, 7.64; N, 5.71.

B) Ethyl 5-(p-chlorobenzoyl)-1,4-dimethyl -3-ethoxycarbonylpyrrole-2-acetate

A solution of 17.5 g. (0.1 mole) p-chlorobenzoyl chloride and 13.3 g. (0.1 mole) aluminum chloride in 150 ml. of dichloroethane is added rapidly to a solution of 25.3 g. (0.1 mole) of ethyl 1.4-dimethyl-3-ethoxycarbonylpyrrole-2-acetate in 100 ml. of refluxing 1,2-dichloroethane. The solution is refluxed for 3.5 hours and poured into ice-hydrochloric acid. The organic layer is separated, and the aqueous layer washed with 1,2-dichloroethane. The combined organics are washed successively with water, N,N-dimethylaminopropylamine, dilute HCl and brine. The solution is then dried over anhydrous magnesium sulfate, and the solvent evaporated in vacuo. The residue product is crystallized from cyclohexane and recrystallized from methanol to give ethyl 5-(p-chlorobenzoyl)-1,4 dimethyl-3-ethoxycarbonylpyrrole-2-acetate as a white solid, M.P. 91°–93° C.

C) 5-(p-chlorobenzoyl)-3-carboxy-1,4-dimethylpyrrole-2-acetic acid

A suspension of 17.3 g. (0.0435 mole) of ethyl 5-(p-chlorobenzoyl)-1,4 dimethyl-3-ethoxypyrrole-2-acetate in 170 g. of 25% sodium hydroxide is heated under reflux for 3 hours. The suspension is poured into ice, and the resulting yellow solution is added to ice-hydrochloric acid with stirring. The precipitated solid is collected by filtration, air dried and recrystallized from acetone, containing 10% water to give 5-(p-chlorobenzoyl)-3-carboxy-1.4-dimethylpyrrole-2-acetic acid as a white solid, M.P. 253°–254° C.

D) Ethyl-5-(p-chlorobenzoyl)-3-carboxy-1,4-dimethylpyrrole-2-acetate

A suspension of 2.0 g. of 5-(p-chlorobenzoyl)-3-carboxyl-1,4-dimethylpyrrole-2-acetic acid in 20 ml. of 0.5% ethanolic hydrogen chloride is heated under reflux. The solid gradually dissolves. After 40 minutes a white crystalline solid precipitates. The solution is cooled, and the solid product, ethyl 5-(p-chlorobenzoyl)-3-carboxy-1,4-dimethylpyrrole-2-acetate, is filtered and dried, M.P. 197°–198° C.

E) Ethyl-5-(p-chlorobenzoyl)-1,4-dimethylpyrrole-2-acetate

A 9.0 g. (0.0255 mole) sample of ethyl 5-(p-chlorobenzoyl)-3-carboxyl-1,4-dimethylpyrrole-2-acetate is heated under nitrogen at 210° to 230° C. for 2 hours. Gas is evolved. The residue is molecularly distilled in a sublimator at 195° C., 0.05 mm./Hg. The sublimate is recrystallized from cyclohexane to give ethyl 5-(ρ-chlorobenzoyl)-1,4-dimethylpyrrole-2-acetate as a white solid, M.P. 107°–109° C.

F) 5-(ρ-chlorobenzoyl)-1,4-dimethylpyrrole-2-acetic acid

A suspension of 4.0 g. (0.0125 mole) of ethyl 5-(ρ-chlorobenzoyl)-1,4-dimethylpyrrole-2-acetate in 26 ml. of 0.5N sodium hydroxide (0.013 mole) is heated under reflux for 30 mins. The resulting solution is acidified with dilute hydrochloric acid, and the precipitated solid is collected by filtration, air dried and recrystallized from 2-propanol to give 5-(ρ-chlorobenzoyl)-1,4-dimethylpyrrole-2-acetic acid as a white crystalline solid, M.P. 178°–179° C.

Analysis-Calcd. for $C_{15}H_{14}ClNO_3$ (percent): C, 61.76; H, 4.83; N, 4.82 Found (percent): C, 61.68; H, 4.96; N, 4.89.

G) Poly-N-[5-(ρ-Chlorobenzoyl) 1,4 Dimethyl Pyrrole-2-Acetyl] Chitosan 5-(ρ-chlorobenzoyl)-1,4 dimethyl pyrrole-2-acetic acid (0.01 mol.) is conjugated to chitosan (0.01 mol-$NH_2$) according to Scheme V. Specifically, isobutyl chlorocarbonate is used with triethyl amine the tertiary amine. The procedure yields the desired compound ($R_1=CH_3$; $R_2=$ρ-chlorobenzoyl; $R_3=$hydrogen; $R_4=CH_3$; Q=chitosan; m=1; n=0; q>40; p/q>0.8; p>32.)

EXAMPLE 20

Poly-N-[5-(ρ-Chlorobenzoyl)-1-Methylpyrrole-2-Acetyl] Chitosan

A) Ethyl 5-(ρ-chlorobenzoyl)-1-methylpyrrole-2-acetate

To a solution of 220.5 g. (0.131 mole) of ethyl-N-methylpyrrole-2-acetate and 24.5 g. (0.14 mole) of ρ-chlorobenzoyl chloride in 120 ml. of carbon disulfide is added 35.0 g. (0.262 mole) of anhydrous aluminum chloride over a period of 20 minutes with intermittent cooling to keep the temperature at 25° C. The mixture is stirred for an additional 20 minutes. The carbon disulfide solvent is then decanted and discarded. The red gummy residue is washed with hexane and dilute hydrochloric acid and ice is added to the mixture. The mixture is extracted with ether. The ether solution is shaken with an aqueous solution of dimethylaminopropylamine and washed with dilute hydrochloric acid followed by brine. The solution is dried over magnesium sulfate and treated with charcoal. After removal of the charcoal, the solvent is evaporated in vacuo leaving a partially crystalline red oil as a residue. This material is extracted with three 500 ml. portions of boiling pentane. The combined pentane extracts are evaporated in vacuo, and the residue is crystallized from 60 ml. of cold methanol. The resulting solid is collected and washed with cold methanol; there is obtained about 6.3 g. of white crystalline solid, ethyl-5-(ρ-chlorobenzoyl)-1-methylpyrrole-2-acetate, M.P. 74°–76° C. Recrystallization from methyl cyclohexane raises the melting point to 78°–80° C.

B) 5-(ρ-chlorobenzoyl)-1-methylpyrrole-2-acetic acid and its sodium salt

A suspension of 3.06 g. (0.01 mole) of ethyl-5-(ρ-chlorobenzoyl)-1-methylpyrrole-2-acetate in 25 ml. of 0.5N sodium hydroxide is refluxed for 30 minutes. About two-thirds of this solution is cooled, washed with ether, and then acidified with dilute hydrochloric acid. The resulting solid precipitate is collected by filtration, dried and recrystallized from ethanol-water to give the product, 5-(ρ-chlorobenzoyl)-1-methylpyrrole-2-acetic acid; M.P. 189°–191° C. Upon recrystallization from ethanol-water, the melting point is 188°–190° C. The other one-third of the solution is cooled in an ice-bath whereupon the yellow sodium salt of the acid is precipitated and collected by filtration.

Analysis-Calcd. for $C_{14}H_{12}ClNO_2$ (percent); C, 60.54; H, 4.36; N, 5.05 Found (percent); C, 60.54; H, 4.37; N, 5.14.

C) Poly-N-[5-(ρ-Chlorobenzoyl)-1-Methylpyrrole-2-Acetyl] Chitosan 5-(ρ-chlorobenzoyl)-1-methylpyrrole-2-acetic acid (0.01 mol.) is conjugated to chitosan (0.01 mol-$NH_2$) according to Scheme V. Specifically, (A) is used with (B) the tertiary amine. The procedure yields the desired compound ($R_1=CH_3$; $R_2=$ρ-chlorobenzoyl; $R_3=$hydrogen; n=0; m=1; Q=chitosan; q>40; p/q>0.8; p>32.)

EXAMPLE 21

Poly-ε-[5-(ρ-toluoyl)-1-methylpyrrole-2-acetyl] polylysine

A) 5-(ρ-toluoyl)-1-methylpyrrole-2-acetonitrile

To a cooled suspension of 26.6 g. (0.2 mole) aluminum chloride in 80 ml. dichloroethane is added dropwise 30.8 g. (0.2 mole) ρ-toluoyl chloride. The resulting solution is added dropwise to a solution of 1-methylpyrrole-2-acetonitrile in 80 ml. dichloroethane cooled externally with an ice bath. After the addition, the resulting solution is stirred at room temperature for twenty minutes and then refluxed for three minutes. The solution is poured into ice acidified with dilute hydrochloric acid. The organic and aqueous fractions are separated. The aqueous fraction is extracted once with chloroform. The organic fractions are combined and washed successively with N,N-dimethyl-1,3-propanediamine, dilute hydrochloric acid, saturated sodium bicarbonate solution and saturated sodium chloride solution. The organic fraction is dried over anhydrous magnesium sulfate. The solvent is then evaporated off. Upon trituration of the residue with methanol, a solid crystallizes, 5-(ρ-toluoyl)-1-methylpyrrole-2-acetonitrile, which is removed by filtration and purified by recrystallization from benzene. Additional product is isolated from the mother liquors which are combined, concentrated in vacuo and the resulting oily residue column chromatographed on neutral alumina using hexane, benzene and ether as successive solvents. The product is isolated by concentrating in vacuo the first few major compound-bearing fractions (10% ether in benzene). The solids are combined and recrystallized from methanol, and then from benzene-hexane, M.P. 102°–105° C.

B) 5-(ρ-toluoyl)-1-methylpyrrole-2-acetic acid

A solution of 3.67 g. (0.015 mole) of 5-(ρ-toluoyl)-1-methyl-pyrrole-2-acetonitrile, 24 ml. of 1N sodium hydroxide, and 50 ml. of 95% ethanol is stirred and refluxed for twenty-four hours. The resulting solution is poured into ice acidified with dilute hydrochloric acid. A white solid precipitates which is extracted into ether. The ether phase is washed with a saturated solution of sodium chloride and dried over anhydrous magnesium sulfate. The solvent is evaporated and a white solid, 5-ρ-toluoyl)-1-methylpyrrole-2-acetic acid, is obtained which is recrystallized twice from isopropanol, M.P., 155°–157° C.

C) Poly-ε-[5-(ρ-toluoyl)-1-methyl-acetyl] polylysine 5-(ρ-toluoyl)-1-methyl-acetic acid (0.01 mol.) is conjugated to polylysine (0.01 mol-$NH_2$) according to Scheme II. The procedure yields the desired compound ($R_1=$methyl; $R_2=$ρ-toluoyl; $R_3=$hydrogen; n=0; m=1; Q=polylysine; q>50; p/q>0.9; p>45.)

EXAMPLE 22

Poly-N-[5-(ρ-anisoyl)-1-methylpyrrole-2-acetyl] chitosan

A) Methyl 5-(ρ-anisoyl)-1-methylpyrrole-2-acetate

A solution of 17.0 g. (0.1 mole) of ρ-anisoyl chloride and 13.3 g. (0.1 mole) of aluminum chloride in 200 ml. of methylene chloride is added over 5 minutes to a solution of methyl 1-methylpyrrole-2-acetate in 100 ml. of methylene chloride at ice bath temperature. The mixture is stirred for 25 minutes and poured into ice acidified with dilute hydrochloric acid. The organic layer is separated, and the aqueous layer is washed with methylene chloride. The combined organic solutions are washed successively with dimethylaminopropylamine solution, dilute hydrochloric acid and brine, and then dried over anhydrous magnesium sulfate. The solvent is evaporated in vacuo to give a dark oily residue which is crystallized from 40 ml. of cold methanol, and recrystallized from methanol to give white crystalline methyl 5-(ρ-anisoyl)-methylpyrrole-2-acetate, M.P. 104°–105° C.

B) 5-(ρ-anisoyl)-methylpyrrole-2-acetic acid

A solution of 3.00 g. (0.0105 mole) of methyl 5-(ρ-anisoyl)-1-methylpyrrole-2-acetate in 12 ml. (0.012 mole) of 1N sodium hydroxide solution and 5 ml. of 95% ethanol is refluxed for 30 minutes. The solution is diluted with water and the ethanol is evaporated in vacuo. The solution is filtered, and the filtrate acidified with dilute hydrochloric acid. The precipitated solid is collected by filtration, dried and recrystallized from methanol-water to give about 2.4 g. (87% yield) of white-5-(ρ-anisoyl)-1-methylpyrrole-acetic acid, M.P. 170°–171° C.

Analysis-Calcd. for $C_{15}H_{15}NO_4$ (percent): C, 65.92; H, 5.53; N, 5.13. Found (percent): C, 66.01; H, 5.62; N, 5.12.

C) Poly-N-[5-(ρ-anisoyl)-1-methylpyrrole-2-acetyl] chitosan

5-ρ(anisoyl)-1-methyl pyrrole acetic acid (0.01 mol.) is conjugated to chitosan (0.01 mol-$NH_2$) according to Scheme V. Specifically, diethyl chlorocarbonate is used with triethyl amine. The procedure yields the desired compound ($R_1$=$CH_3$; $R_2$=ρ-anisoyl; $R_3$=hydrogen; Q=chitosan; n=0; m=1; q>40; p/q>0.8; p>32.)

EXAMPLE 23

Poly [5-(ρ-aminobenzoyl)-1-methylpyrrole-2-acetyl] polyvinyl alcohol

A) 5-(ρ-nitrobenzoyl)-1-methylpyrrole-2-acetonitrile

A solution of 46.4 g. (0.25 mole) of ρ-nitrobenzoyl chloride in 100 ml. 1,2-dichloroethane is added portionwise to a suspension of 32.2 g. (0.25 mole) aluminum chloride in 100 ml. 1,2-dichloroethane. This mixture is added dropwise to a chilled solution of 30.0 g. (0.25 mole) 1-methylpyrrole-2-acetonitrile in 100 ml. 1,2-dichloroethane. After the addition is complete, the mixture is stirred for twenty minutes at room temperature, and then refluxed for four times. It is poured into ice acidified with 3N hydrochloric acid. The organic phase is separated and washed successively with N, N-dimethyl-1,3-propanediamine, 3N hydrochloric acid and saturated sodium chloride solution. It is then dried over magnesium sulfate and the solvent evaporated in vacuo. The resulting semi-solid residue is triturated with cold methanol from which the product, 5-(ρ-nitrobenzoyl)-1-methylpyrrole-2-acetonitrile, crystallizes. It is removed by filtration and purified by recrystallization from acetone, M.P. 167°–169° C.

B) 5-(ρ-aminobenzoyl)-1-methylpyrrole-2-acetonitrile

A solution of 7 g. (0.026 mole) of 5-(ρ-nitrobenzoyl)-1-methylpyrrole-2-acetonitrile in 450 ml. of ethyl acetate containing 1 g. palladium-on-carbon catalyst is hydrogenated in a Parr shaker under 44 psi of hydrogen until the theoretical amount of hydrogen is consumed. The catalyst is filtered off, and the solvent evaporated in vacuo. About 6.0 g. (97% yield) of a yellow solid, 5-(ρ-aminobenzoyl)-1-methylpyrrole-2-acetonitrile remains, M.P. 137°–142° C.

C) 5-(ρ-aminobenzoyl)-1-methylpyrrole-2-acetic acid

A suspension of 6.0 g. (0.025 mole) of 5-(ρ-aminobenzoyl)-1-methylpyrrole-2-acetonitrile, 25 ml. 95% ethanol and 25 ml. 1N sodium hydroxide is refluxed overnight. The ethanol is then evaporated in vacuo and the remaining suspension is poured into ice acidified with dilute hydrochloric acid to pH 5. The resulting solid is partitioned between sodium bicarbonate solution and chloroform. The insoluble substances are filtered from the two-phase mixture. The sodium bicarbonate layer is separated and acidified slowly with dilute hydrochloric acid. Solids precipitate at various pHs which are separated by filtration. The desired product, 5-(ρ-aminobenzoyl)-1-methyl-pyrrole-2-acetic acid, precipitates at Ph 3, M.P. 173°–175° C.

D) Poly-[5-(ρ-aminobenzoyl-1-methylpyrrole-2-acetyl] polyvinyl alcohol 5-(ρ-aminobenzoyl-1-methyl pyrrole-2-acetic acid (0.01 mol.) is conjugated to polyvinyl alcohol (0.01 mol-OH) according to Scheme III. Specifically, triisopropylamine is used as the base. The procedure yields the desired compound ($R_1$=$CH_3$; $R_2$=ρ-aminobenzoyl; $R_3$=hydrogen; Q=polyvinyl alcohol; n=0; m=1; q>100; p/q>0.8; p>80.)

EXAMPLE 24

Poly-ε-[5-(ρ-chlorobenzoyl)-α-methyl-1-methylpyrrole-2-acetyl] polylysine

A) Ethyl-5-(ρ-chlorobenzoyl)-α-methyl-1-methylpyrrole-2-acetate

A solution of 6.68 g. (0.0219 mole) of ethyl 5-(ρ-chlorobenzoyl)-1-methylpyrrole-2-acetate in 50 ml. of ether is added to a solution of 0.94 g. (0.024 mole) of sodamide in about 150 ml. of liquid ammonia at –33° C. The mixture is allowed to reflux for 15 minutes and 3.10 g. (0.0219 mole) of methyl iodide is added. The mixture is stirred for one hour; then the ammonia is allowed to boil off. Ether and enough ammonium chloride to neutralize any anion are added. The mixture is poured into dilute hydrochloric acid and the ether solution is separated and washed with sodium bisulfite solution, sodium bicarbonate solution and brine. It is dried over anhydrous magnesium sulfate and evaporated to give about 6.8 g. of an oily residue which crystallized upon standing. The solid is recrystallized successively from cyclohexane and methanol to give a white crystalline solid, ethyl 5-(ρ-chlorobenzoyl)-α-methyl-1-methylpyrrole-2-acetate, M.P. 67°–68° C.

B) 5-(ρ-chlorobenzoyl)-α-methyl-1-methylpyrrole-2-acetic acid

A solution of 4.05 g. (0.0126 mole) of ethyl 5-(ρ-chlorobenzoyl)-α-methyl-1-methylpyrrole-2-acetate, 15 ml. of 1N sodium hydroxide solution and 2 ml. of ethanol is refluxed for 30 minutes. The solution is cooled, diluted with water and filtered. The filtrate is acidified with dilute hydrochloric acid. The precipitates solid is collected and recrystallized from methanol-water to give a white crystalline solid, 5-(ρ-chlorobenzoyl)-α-methyl-1-methylpyrrole-2-acetic acid, M.P. 135°–136° C.

Analysis-Calcd. for $C_{28}H_{14}ClNO_3$ (percent): C, 61.76; H, 4.83; N, 4.82. Found (percent): C, 61.68; H, 4.86; N, 4.89.

C) Poly-ε-[5-(ρ-chlorobenzoyl)-α-methyl-1-methylpyrrole-2-acetyl] polylysine 5-(ρ-chlorobenzoyl)-α-methyl-1-methylpyrrole-2-acetic acid (0.01 mol.) is conjugated to polylysine (0.01 mol-$NH_2$) according to Scheme IV. Specifically, thionylchloride is used to prepare the acid chloride of 5-(ρ-chlorobenzoyl)-α-methyl-1-methylpyrrole-2-acetic acid. Pyridine is the base. The procedure yields the desired compound ($R_1$=$CH_3$; $R_2$=ρ-chlorobenzoyl; $R_3$=$CH_3$; m=1; Q=polylysine; n=0; q>50; p/q>0.8; p>40.)

EXAMPLE 25

Poly [5-(ρ-chlorobenzoyl)-1-methylpyrrole- 2 acetyl] polyvinyl alcohol

A) 5-(m-chlorobenzoyl)-1-methylpyrrole -2-acetonitrile

To a cooled suspension of 16.6 g. (0.12 mole) aluminum chloride in 60 ml. 1,2-dichlorobenzoylchloride is added dropwise 23 g. (0.12 mole) m-chlorobenzoylchloride. The resulting suspension is added dropwise to a cooled solution of 15 g. (0.12 mole) 1-methylpyrrole-2-acetonitrile in 60 ml. 1,2-dichloroethane. The reaction mixture is stirred for about twenty minutes at room temperature and then heated and refluxed for three minutes. The reaction is terminated by pouring the mixture into ice acidified with 3N hydrochloric acid. The resulting two fractions are separated. The aqueous fraction is washed with chloroform. The organic fraction is then dried over anhydrous magnesium sulfate. The solvent is evaporated, and the resulting residue is triturated with cold methanol to yield a precipitate of the desired product which is filtered off and set aside. The methanol filtrate is concentrated in vacuo and the remaining oily residue is chromatographed on a column packed with neutral alumina using hexane, benzene and ether as the successive solvents. About 2.5 g. of the desired product are isolated by evaporation of the first few compound-bearing (ether) fractions. The solids are combined and recrystallized from methanol to yield about 3.6 g. of 5-(m-chlorobenzoyl)-1-methylpyrrole-2-acetonitrile, M.P. 122°–127° C.

Analysis-Calcd. for $C_{14}H_{11}ClN_3O$ (percent): N, 10.83. Found (percent): N, 10.52.

B) 5-(m-chlorobenzoyl)-1-methylpyrrole -2-acetic acid

A mixture of 2.8 g. (0.01 mole) of 5-(m-chlorobenzoyl)-1-methylpyrrole-2-acetonitrile. 22 ml. of 1N sodium hydroxide solution and 5 ml. ethanol is stirred at reflux for 15 hours. Some of the ethanol is evaporated. The remaining solution is poured into ice acidified with dilute hydrochloric acid. A white solid, 5-(m-chlorobenzoyl)-1-methylpyrrole-2-acetic acid, precipitates which is recrystallized twice from methanol water, M.P. 165° C.

Analysis-Calcd. for $C_{14}H_{18}ClN_3O$ (percent): C, 60.54; H, 4.36; N, 5.05. Found (percent): C, 60.61; H, 4.40; N, 4.87.

C) Poly [5-(ρ-chlorobenzoyl)-1-methylpyrrole -2 acetyl] polyvinyl alcohol 5-(ρ-chlorobenzoyl)-1-methylpyrrole-2-acetic acid (0.01 mol.) is conjugated to polyvinyl alcohol (0.01 mol-OH) according to Scheme IV. Specifically, oxalylchloride is used to prepare the acid chloride of 5-(ρ-chlorobenzoyl)-1-methylpyrrole-2-acetic acid. Triethyl amine is the base. The procedure yields the desired compound ($R_1$=1—$CH_3$; $R_2$=5-ρ-chlorobenzoyl; $R_3$=hydrogen; $R_5$=hydrogen; m=1; Q=polyvinyl alcohol; n=0; q>50; p/q>0.8; p>40.)

EXAMPLE 26

Poly [5-(ρ-chlorobenzoyl)-1-methylpyrrole-2-propionyl] polyvinyl alcohol

A) Ethyl 2-(1-methyl-2-pyrrolyl)-propionate

A solution of 62.4 g. (0.35 mole) ethyl 2-(1-methyl-2-pyrrolyl)-acrylate in 350 ml. 95% ethanol is hydrogenated in a Parr shaker using 3 g. of platinum oxide as the catalyst. The hydrogenation is continued overnight under 32 p.s.i. of hydrogen. The mixture is filtered, and the filtrate concentrated in vacuo. The residual yellow oil is dissolved in ether and washed successively with 3N hydrochloric acid, saturated sodium bicarbonate solution and saturated sodium chloride solution. The ether solution is dried over anhydrous magnesium sulfate. The ether solvent is then evaporated to yield about 42 g. of a clear oil, ethyl 2-(1-methyl-2-pyrrolyl)-propionate.

B) Ethyl 5-(ρ-chlorobenzoyl)-1-methylpyrrole-2-propionate

To a suspension of 26.6 g. (0.2 mole) of aluminum chloride in 100 ml. methylene chloride is added 34.8 g. (0.2 mole) of ρ-chlorobenzoyl chloride. The resulting solution is added dropwise to a solution of 36.8 g. (0.2 mole) of ethyl 2-(1-methyl-2-pyrrolyl)propionate in 100 ml. methylene chloride while cooling externally with an ice bath. After the addition is complete, the reaction is stirred for 10 minutes and poured into ice acidified with dilute hydrochloric acid. The two fractions are separated. The organic fraction is washed successively with N,N-dimethyl-1,3-propanediamine, 3N hydrochloric acid, saturated sodium bicarbonate solution and saturated sodium chloride solution. The organic fraction is then dried over anhydrous magnesium sulfate, and the solvent evaporated in vacuo. A solid is crystallized in the resulting oily residue which is isolated and purified by recrystallization from methanol to yield ethyl 5-(ρ-chlorobenzoyl)-1-methylpyrrole-2-propionate, M.P. 71.5°–73° C.

C) 5-(ρ-chlorobenzoyl)-1-methylpyrrole-2-propionic acid

A suspension of 8.0 g. (0.025 mole) of ethyl 5-(ρ-chlorobenzoyl)-1-methylpyrrole-2-propionate in 15 ml. ethanol and 30 ml. 1N sodium hydroxide is refluxed for one hour. The ethanol is then evaporated, and the remaining solution is poured into dilute hydrochloric acid. The remaining solution is poured into dilute hydrochloric acid. The resulting white precipitate is filtered off and purified by recrystallization from isopropyl alcohol, 5-(ρ-chlorobenzoyl)-1-methylpyrrole-2-propionic acid, M.P. 188°–191° C.

D) Poly [5-(ρ-chlorobenzoyl)-1-methylpyrrole-2-propionyl] polyvinyl alcohol 5-(ρ-chlorobenzoyl)-1-methylpyrrole-2 propionic acid (0.01 mol.) is conjugated to polyvinyl alcohol (0.01 mol-OH) according to Scheme III. Specifically, thiethylamine is used as the base. The procedure yields the desired compound ($R_1$=$CH_3$; $R_2$=ρ-chlorobenzoyl; $R_3$=hydrogen; $R_5$=hydrogen; m=2; n=0; Q=polyvinyl alcohol; q>100; p/q>0.8; p>80.)

EXAMPLE 27

Poly-ε-[5-(ρ-chlorobenzoyl)-4-methylpyrrole-3-acetyl] polylysine

A) Ethyl 5-(ρ-chlorobenzoyl)-2,4-dimethylpyrrole-3-acetate

To a solution of 29 g. (0.17 mole) of ρ-chlorobenzoyl chloride and 28.0 g. (0.15 mole) of ethyl 2,4-dimethylpyrrole-3-acetate in 100 ml. carbon disulfide, is added 41.23 g. (0.31 mole) of anhydrous aluminum chloride. The reaction mixture is cooled externally with an ice bath. The mixture is stirred for 15 minutes after which the solvent is decanted, and the remaining solid treated with ice acidified with 3N hydrochloric acid. The acid mixture is extracted three times with ether. The combined ether extracts are washed successively with N,N-dimethyl-1,3-propanediamine, 3N hydrochloric acid, and a saturated solution of sodium chloride. The solution is dried over anhydrous magnesium sulfate, and the solvent evaporated in vacuo. The remaining solid is recrystallized from methanol to yield, ethyl 5-(ρ-chlorobenzoyl)-2,4-dimethylpyrrole-3-acetate, M.P. 126°–129° C.

B) Ethyl 5-(ρ-chlorobenzoyl) 1-methyl-2-trichloromethylpyrrole-3-acetate

To a suspension of 9.6 g. (0.03 mole) of ethyl 5-(ρ-chlorobenzoyl)-2,4-dimethylpyrrole-3-acetate in 75 ml. ether is added dropwise 7.8 ml. sulfurylchloride, cooling externally with an ice bath. The resulting suspension is stirred at room temperature for 15 hours. The resulting white solid, ethyl 5-(ρ-chlorobenzoyl)-4-methyl-2-trichloromethylpyrrole-3-acetate, is filtered and purified by recrystallization twice from methylcyclohexane, M.P. 133°–137° C.

C) 5-(ρ-chlorobenzoyl)-4-methyl-2 carboxypyrrole-3-acetic acid

A solution of 1.0 g. (0.0026 mole) of ethyl 5-(ρ-chlorobenzoyl)-4-methyl-2-trichloromethylpyrrole-3-acetate in 10 ml. dioxane and 3 ml. water is refluxed for three hours. The resulting solution is cooled and extracted with chloroform. The organic fraction is extracted with a saturated solution of sodium bicarbonate. The aqueous phase is made acidic with dilute hydrochloric acid, and the resulting precipitate of 5-(ρ-chlorobenzoyl)-4-methyl-2-carboxypyrrole-3-acetic acid is filtered and dried, M.P. 240° C.

D) 5-(ρ-chlorobenzoyl)-4-methylpyrrole-3-acetic acid

A solution of 1.4 g. (0.004 mole) of 5-(ρ-chlorobenzoyl)-4-methyl-2-carboxypyrrole-3-acetic acid in 25 ml. quinoline is heated overnight at 160° C. under nitrogen. The reaction is poured into ice acidified with hydrochloric acid. The mixture is extracted with chloroform, and the organic phase is extracted with a saturated solution of sodium bicarbonate. The basic solution is made acidic with dilute hydrochloric acid, and the resulting solid, 5-(ρ-chlorobenzoyl)-4-methylpyrrole-3-acetic acid, is filtered and purified by recrystallization from isopropyl alcohol, M.P. 145°–147° C.

E) Poly-ε-[5-(ρ-chlorobenzoyl)-4-methylpyrrole-3-acetyl] polylysine 5-(ρ-chlorobenzoyl)-4-methyl-pyrrole-3-acetic acid (0.01 mol.) is conjugated to polylysine (0.01 mol-$NH_2$) according to Scheme IV. Specifically, oxalylchloride is used to prepare the acid chloride of 5-(ρ-chlorobenzoyl)- 4-methyl-pyrrole-3-acetic acid. Pyridine is the base. The procedure yields the desired compound ($R_1$=$CH_3$; $R_2$=ρ-chlorobenzoyl; $R_3$=hydrogen; $R_5$=hydrogen; Q=polylysine; n=0; m=1; q>50; p/q>0.8; p>40.)

EXAMPLE 28

Poly-ε-[5-isopropylbenzoyl-1-methylpyrrole-2-acetyl] polylysine

A) 5-(ρ-isopropylbenzoyl)-1-methylpyrrole-2-acetonitrile

To a suspension of 17.5 g. (0.131 mole) aluminum chloride in 60 ml. 1,2-dichloroethane is added 24 g. (0.131 mole) ρ-isopropylbenzoyl chloride. The resulting mixture is added slowly and dropwise to a chilled solution (0° C.) of 15.7 g. (0.131 mole) 1-methylpyrrole-2-acetonitrile in 100 ml. of 1,2-dichloroethane. After addition is complete, the mixture is stirred at room temperature for twenty minutes and heated at reflux for three minutes. The reaction mixture is then cooled and poured into ice-dilute hydrochloric acid. The organic phase is separated and washed successively with N,N-dimethyl-1,3-propanediamine, dilute hydrochloric acid and a saturated solution of sodium chloride; dried over magnesium sulfate; and the solvent evaporated. The product, 5-(ρ-isopropylbenzoyl)-1-methylpyrrole-2-acetonitrile, is isolated from the residual oil by column chromatography. The column is packed with acid washed alumina and eluted with benzene, ether and ethylacetate. The product is found in the first compound-bearing fraction which absorbs ultraviolet light at approximately 250 m. It is purified by recrystallization twice in ether:pentane (9 g.; 20% yield), M.P. 59°–64° C.

Analysis-Calcd. for $C_{17}H_{18}N_2O$ (percent): N, 10.53. Found (percent): N, 10.71.

B) 5-(ρ-isopropylbenzoyl)-1-methylpyrrole-2-acetic acid

A solution of 6.5 g. (0.024 mole) of 5-(ρ-isopropylbenzoyl)-1-methylpyrrole-2-acetonitrile, 52 ml. 1N sodium hydroxide and 50 ml. 95% ethanol are heated at reflux overnight. The ethanol is then evaporated, and the remaining yellow solution is poured into ice-dilute hydrochloric acid. A precipitate forms which is separated by filtration and recrystallized in ether:hexane. The solid is then partitioned between sodium bicarbonate solution and ether. The sodium bicarbonate phase is separated and acidified with dilute hydrochloric acid. The white precipitate, 5-(ρ-isopropylbenzoyl)-1-methylpyrrole-2-acetic acid, is filtered and dried in vacuo (4.0 g., 58% yield), M.P. 98°–101° C.

Analysis-Calcd. for $C_{11}H_{10}N)_1$ (percent): N, 4.91. Found (percent): N, 5.14.

C) Poly-ε-[5-isopropylbenzoyl-1-methylpyrrole-2-acetyl] polylysine 5-(ρ-isopropylbenzoyl)-1-methyl-pyrrole-2-acetic acid (0.01 mol.) is conjugated to polylysine (0.01 mol-$NH_2$) according to Scheme V. Specifically, isobutylchlorocarbonate is used with triethyl amine the tertiary amine. The procedure yields the desired compound ($R_1$=$CH_3$; $R_2$=isopropylbenzoyl; $R_3$=hydrogen; $R_5$=hydrogen; Q=polylysine; m=1; n=0; q>50; p/q>0.9;p>45.)

EXAMPLE 29

Poly [1,4-dimethyl-5-(ρ-toluoyl)-pyrrole-2-acetyl] polyvinyl alcohol

A) Ethyl 1,4-dimethyl-3-ethoxycarbonyl-5-(ρ-toluoyl)-pyrrole-2-acetate

A solution of 30.8 g. ρ-toluoyl chloride and 26.6 g. (0.2 mole) of aluminum chloride in 250 ml. of 1,2-dichloroethane is added to a refluxing solution of 50.6 g. (0.2 mole) of ethyl 3-ethoxycarbonyl-1,4-dimethylpyrrole-2-acetate in 250 ml. of 1,2-dichloroethane over 30 min. The mixture is heated under reflux for 90 min. and poured into ice-dilute hydrochloric acid. The organic solution is separated, washed with brine, and dried over magnesium sulfate. The solven is evaporated in vacuo, and the residue is recrystallized from methanol to give ethyl 1,4-dimethyl-3-ethoxycarbonyl-5-(ρ-toluoyl)-pyrrole-2-acetate as a white solid, M.P. 108°–111° C.

B) 3-carboxy-1,4-dimethyl-5-(ρ-toluoyl)-pyrrole-2-acetic acid

A suspension of 54 g. (0.145 mole) of ethyl 1,4-dimethyl-3-ethoxycarbonyl-5-(ρ-toluoyl) pyrrole-2-acetate in 500 g. of 25% sodium hydroxide is heated at just below reflux for 3 hours. The yellow suspension is then poured into ice-hydrochloric acid, and the preciptated solid is collected, air dried and recrystallized from acetone-water to give 3-carboxy-1,4-dimethyl-5-(ρ-toluoyl)-pyrrole-2-acetic acid as a white solid, M.P. 229°–230° C.

Analysis-Calcd. for $C_{17}H_{15}NO_5$ (percent): C, 64.75; H, 5.43; N, 4.44. Found (percent) C, 64.86; H, 5.53; N, 4.47.

C) Ethyl 3-carboxy-1,4,-dimethyl-5-(ρ-toluoyl)-pyrrole-2-acetate

A solution of 37 g. (0.118 mole) of 3-carboxy-1,4-dimethyl-5-(ρ-toluoyl)-pyrrole-2-acetic acid in 370 ml. of ethanol containing 1.8 g. of dry hydrogen chloride is heated under reflux for 45 min. The solution is cooled, and the solid which recipitated, ethyl 3-carboxy-1,4-dimethyl-5-(ρ-toluoyl)-pyrrole-2-acetetate, is collected, M.P. 200°–202° C.

D) Ethyl 1,4-dimethyl-5-(ρ-toluoyl)-pyrrole-2-acetate

A solution of 330 g. (0.096 mole) of ethyl 3-carboxy-1,4-dimethyl-5-(ρ-toluoyl)-pyrrole-2-acetate in 200 ml. of quinoline with 0.1 gm copper chromite added is heated under nitrogen for six hours at 200° C. then for 30 mins. at 220° C. The quinoline is distilled off in vacuo. The residue is dissolved in ether and washed successively with dilute hydrochloric acid, dilute sodium hydroxide, and brine; dried over magnesium sulfate; and the solvent evaporated in vacuo to give a brown oily residue which crystallizes. It is recrystallized from methanol, sublimed at 150° C. (0.025 mm./Hg) and recrystallized from hexane to give ethyl 1,4-dimethyl-5-(ρ-toluoyl)-pyrrole-2-acetate as a white solid, M.P. 90°–93° C.

E) 1,4-dimethyl-5-(ρ-toluoyl)-pyrrole-2-acetic acid

A suspension of 8.5 g. (0.0284 mole) of ethyl 1,4 dimethyl-5-(ρ-toluoyl)-pyrrole-2-acetate in 29 ml. of 1N sodium hydroxide solution is heated under reflux for 20 min. The yellow solution is diluted with water and added to dilute hydrochloric acid. The precipitated solid is collected, dried in vacuo and recrystallized from 2-propanol to give 1,4 dimethyl-5-(ρ-toluoyl)-pyrrole-2-acetic acid as a white solid, M.P. 160°–161° C.

Analysis-Calcd. for $C_{14}H_{17}NO_3$ (percent; C, 70.83; H, 6.32; N, 5.16. Found (percent): C, 70.90; H, 6.39, N, 5.25.

F) Poly [1,4-dimethyl-5-(ρ-toluoyl)-pyrrole-2-acetyl] polyvinyl alcohol 1,4-dimethyl-5-(ρ-toluoyl)-pyrrole-2-acetic acid (0.01 mol.) is conjugated to polyvinyl alcohol (0.01 mol-OH) according to Scheme IV. Specifically, oxalylchloride is used to prepare the acid chloride of 1,4-dimethyl-5-(ρ-toluoyl)-pyrrole-2-acetic acid. Pyridine is the base. The procedure yields the desired compound ($R_1=CH_3$; $R_2=$ρ-toluoyl; $R_3=$hydrogen; $R_5=CH_3$; Q=polyvinyl alcohol; m=1; n=0; q>50; p/q>0.8; p >40.)

EXAMPLE 30

Poly [5-(ρ-chlorobenzoyl)-4-ethyl-1-methylpyrrole-2-acetyl] methyl cellulose

A) 1-chloro-2-butanone

Chlorination of methylethylketone is carried out according to Bruylant and Houssiau Bull. Soc. Chem. Belg. 6, 492 (1952). The mixture obtained is fractionally distilled at atmospheric pressure through a Vigraeux column. The fraction boiling at 135°–144° C. is shown by vapor phase chromatography to contain approximately 75% 1-chloro-2-butanone and 25% 3-chloro-2-butanone. This fraction may be used in the next reaction without further separation.

B) Ethyl-3-ethoxycarbonyl-4-ethyl-1-methylpyrrole-2-acetate

A 900 ml. solution of 25% aqueous methylamine is cooled in an ice bath and 101 g. (0.5 mole) of diethyl acetone decarboxylate is added. To the mixture is added 110 G. of the 1-chloro-2-butanone mixture obtained in part A. Intermittant cooling is applied to keep the temperature below 60° C. The mixture is stirred for one hour and poured into ice-hydrochloric acid. The crystalline product is collected by filtration and recrystallized from methanol to yield ethyl 3-ethoxycarbonyl-4-ethyl-1-methylpyrrole-2-acetate as a white solid, M.P. 65°–67° C.

C) Ethyl (5-ρ-chlorobenzoyl)-3-ethoxycarbonyl- 4-ethyl-1-methylpyrrole-2-acetate A solution of 13.8 g. (0.0788 mole) of ρ-chlorobenzoyl chloride and 10.5 g. (0.0788 mole) of aluminum chloride in 120 ml. of 1,2-dichloroethane is added to a refluxing soluton of 21.8 (0.0788 mole) of ethyl 3-ethoxycarbonyl-4-ethyl-1-methylpyrrole-2-acetate. The mixture is heated under reflux for 10 hours and stirred at room temperature for an additional 10 hours. It is then poured into ice-hydrochloric acid. The organic layer is separated and the aqueous layer washed with 1,2-dichloroethane. The combined organics are washed successively with water, N,N-dimethylaminopropylamine, dilute HCl and brine. The colution is then dried over anhydrous magnesium solfate and the solven evaporated in vacuo. The residual red oil residue crystallized on standing. It is recrystallized twice from methanol to give ethyl (5-ρ-chlorobenzoyl)-3-ethoxycarbonyl-4-ethyl-1-methylpyrrole-2-acetate as a white solid, M.P. 72°–74° C.

D) 3-carboxy-5-(ρ-chlorobenzoyl)-4-ethyl-1-methylpyrrole-2-acetic acid

A suspension of 18.2 g. (0.044 mole) of ethyl 5-(ρ-chlorobenzoyl)-3-ethoxycarbonyl-4-ethyl-1-methylpyrrole-2-acetate in 170 ml. of 25% aquous sodium, hydroxide solution is heated under reflux for 3 hrs. It is cooled, diluted with water and acidified with dilute hydrochloric acid. The precipitated solid is collected by filtration and air dried. It is recrystallized from acetone-water to give 3-carboxy-5-(ρ-chlorobenzoyl)-4-ethyl-1-methylpyrrole-2-acetic acid, M.P. 211°–212.5° C.

E) Ethyl 3-carboxy-5-(ρ-chlorobenzoyl)-4-ethyl-1-methylpyrrole-2-acetate

A solution of 13.8 g. (0.0375 mole) of 3-carboxy-5-(ρ-chlorobenzoyl)-4-ethyl-1-methylpyrrole-2-acetic acid in 140 ml. of 0.5% ethanolic hydrogen chloride is heated under reflux for 45 min. After cooling, the precipitated solid is collected. A second crop is obtained by partial evaporation of the solvent, recrystallized from ethanol and combined with the first crop to give ethyl-3-carboxy-5-(ρ-chlorobenzoyl)-4-ethyl-1-methylpyrrole-2-acetate. M.P. 185°–186° C.

F) Ethyl 5-(ρ-chlorobenzoyl)-4-ethyl-1-methylpyrrole-2-acetate

A 13.7 g. (0.035 mole) sample of ethyl 3-carboxy-5-(ρ-chlorobenzoyl)-4-ethyl-1-methylpyrrole-2-acetate is heated at 200° to 210° C. under nitrogen for 90 min. The resulting oil is molecularly distilled at 185° C. and 0.1 mm. hexane and then methanol to give ethyl 5-(ρ-chlorobenzoyl)-4-ethyl-1-methylpyrrole-2-acetate as a white solid, M.P. 73°–75° C.

G) 5-(ρ-chlorobenzoyl)-4-ethyl-1-methylpyrrole-2-acetic acid

A suspension of 4.5 g. (0.0136 mole) of ethyl 5-(ρ-chlorobenzoyl)-4-ethyl-1-methylpyrrole-2-acetate in 28 ml. 0.5N sodium hydroxide and 1 ml. of ethanol is heated under reflux for 30 min. The mixture is then poured into ice-dilute hydrochloric acid. The precipitated solid is filtered, air dried and recrystallized from 2-propanol to acetic acid as a white solid, M.P. 129°–131° C.

Analysis-Calcd. for $C_{16}H_{18}ClNO_3$ (percent): C, 62.85; H, 5.29; N, 4.58. Found (percent): C, 62.58, H, 5.40; N, 4.83.

H) Poly [5-(ρ-chlorobenzoyl)-4-ethyl-1-methylpyrrole-2-acetyl] methyl cellulose 5-(ρ-chlorobenzoyl)-4-ethyl-1-methyl-pyrrole-2-acetic acid (0.01 mol.) is conjugated to methyl cellulose (0.01 mol-OH) according to Scheme III. Specifically, triethyl amine is used as the base. The procedure yields the desired compound ($R_1$=ethyl; $R_2$=p-chlorobenzoyl; $R_3$=hydrogen; $R_5$=methyl; Q=methyl cellulose; n=0; m=1; q>50; p/q>0.9; p>45.)

It will be understood that various changes and modifications can be made in the details of procedure, formulation and use without departing from the spirit of the invention, especially as defined in the following claims.

We claim:

1. A compound of the formula:

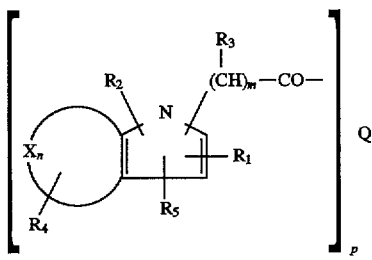

wherein n is 0 or 1, and X represents a condensed phenyl ring;

one of $R_1$ and $R_2$ is independently selected from the group consisting of hydrogen, halogen, lower alkyl; and the other of $R_1$ and $R_2$ is independently selected from the group consisting of substituted or unsubstituted phenyl, benzyl, thienyl, napthyl, pyridyl, furyl, biphenyl, benzoyl, cinnamoyl, thienylcarbonyl, napthylcarbonyl, pyridylcarbonyl, furylcarbonyl or biphenylcarbonyl wherein said substituents are selected from the group consisting of amino, halogen, lower alkyl, lower alkylthio, lower alkoxy or lower haloalkyl;

m is an integer from 1 to 3;

$R_3$ is selected from hydrogen and lower alkyl, or one or more of hydrogen and lower alkyl when m is greater than 1;

$R_4$ is one or more members of the group consisting of hydrogen, lower alkyl, alkoxy, haloalkyl, alkylthio, and halogen;

p is an integer of at least 2;

Q is the depronated residue of a polymer or macromolecular structure having at least two primary and/or secondary amines and/or hydroxy groups; and when n is 0, the structure in formula I represents a substituted pyrrole ring, and $R_5$ is selected from the group consisting of hydrogen, lower alkyl, alkoxy, alkylthio, and halogen; and when n is 1, the structure in the formula represents a substituted indole ring.

2. A compound according to claim 1 wherein n is zero and m is 1.

3. A compound according to claim 2 wherein $R_1$ is a lower alkyl and $R_2$ is selected from substituted phenyl or benzoyl.

4. A compound according to claim 3 wherein said substituents are selected from the group consisting of halogen or lower alkyl.

5. A compound according to claim 4 wherein $R_1$ is on the nitrogen, $R_5$ is in the 4-position and $R_2$ is in the 5-position of said pyrrole ring.

6. The compound according to claim 3 wherein $R_2$ is on the nitrogen, $R_1$ is in the 5-position, and $R_5$ is a lower alkyl in the 2-position on said pyrrole ring.

7. A compound according to claim 1 wherein n is 1 and m is 1.

8. A compound according to claim 7 wherein $R_4$ is lower alkyl or alkoxy.

9. A compound according to claim 8 wherein $R_3$ is hydrogen, and the resulting methyl carboxyl is attached to position 3 of the indole ring; and $R_1$ is a lower alkyl at the 2 position.

10. A compound according to claim 9 wherein $R_2$ is a halo-substituted benzoyl on the nitrogen on the indole ring.

11. A compound according to claim 8 wherein $R_3$ is hydrogen and the resulting methyl carboxyl is on the nitrogen on the indole ring.

12. A compound according to claim 11 wherein $R_3$ is hydrogen and the resulting methyl carbonyl is on the 3-position on the indole ring.

13. A compound according to claim 7 wherein $R_3$ is hydrogen and the resulting methyl carbonyl is on the 3-position on the indole ring.

14. A compound according to claim 13 wherein $R_1$ is lower alkyl attached to position 2; and $R_2$ is selected from the group consisting of benzoyl, cinnamoyl, thionylcarbonyl, napthylcarbonyl, or furylcarbonyl substituted at the nitrogen on the indole ring.

15. A compound according to claim 14 wherein $R_4$ is lower alkyl or lower alkyl at the 5-position on the indole ring.

16. A method for treating patients having colonic polyps to reduce said polyps which comprises administering to said patient a therapeutically effective amount of a compound of the formula:

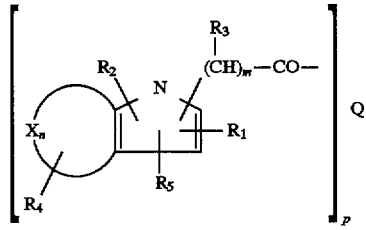

wherein n is 0 or 1, and X represents a condensed phenyl ring;

one of $R_1$ and $R_2$ is independently selected from the group consisting of hydrogen, halogen, lower alkyl; and the other of $R_1$ and $R_2$ is independently selected from the group consisting of substituted or unsubstituted phenyl, benzyl, thienyl, napthyl, pyridyl, furyl, biphenyl, benzoyl, cinnamoyl, thienylcarbonyl, napthylcarbonyl, pyridylcarbonyl, furylcarbonyl or biphenylcarbonyl wherein said substituents are selected from the group consisting of amino, halogen, lower alkyl, lower alkylthio, lower alkoxy or lower haloalkyl;

m is an integer from 1 to 3;

$R_3$ is selected from hydrogen and lower alkyl, or one or more of hydrogen and lower alkyl when m is greater than 1;

$R_4$ is one or more members of the group consisting of hydrogen, lower alkyl, alkoxy, haloalkyl, alkylthio, and halogen;

p is an integer of at least 2;

Q is the depronated residue of a polyamino or polyhydroxy compound; and when n is 0, the structure in formula I represents a substituted pyrrole ring, and $R_5$ is selected from the group consisting of hydrogen, lower alkyl, alkoxy, alkylthio, and halogen; and when n is 1, the structure in the formula represents a substituted indole ring.

17. A method according to claim 16 wherein n is zero and m is 1.

18. A method according to claim 17 wherein $R_1$ is a lower alkyl and $R_2$ is selected from substituted phenyl or benzoyl.

19. A method according to claim 18 wherein said substituents are selected from the group consisting of halogen or lower alkyl.

20. A method according to claim 19 wherein $R_1$ is on the nitrogen, $R_5$ is in the 4-position and $R_2$ is in the 5-position of said pyrrole ring.

21. The method according to claim 18 wherein $R_2$ is on the nitrogen, $R_1$ is in the 5-position, and $R_5$ is a lower alkyl in the 2-position on said pyrrole ring.

22. A method according to claim 16 wherein n is 1 and m is 1.

23. A method according to claim 22 wherein $R_4$ is lower alkyl or alkoxy.

24. A method according to claim 23 wherein $R_3$ is hydrogen, and the resulting methyl carboxyl is attached to position 3 of the indole ring; and $R_1$ is a lower alkyl at the 2 position.

25. A method according to claim 24 wherein $R_2$ is a halo-substituted benzoyl on the nitrogen on the indole ring.

26. A method according to claim 22 wherein $R_3$ is hydrogen, and the resulting methyl carboxyl is on the nitrogen on the indole ring.

27. A method according to claim 26 wherein $R_3$ is hydrogen, and the resulting methyl carboxyl is on the 3-position on the indole ring.

28. A method according to claim 22 wherein $R_3$ is hydrogen, and the resulting methyl carboxyl is on the 3-position on the indole ring.

29. A method according to claim 28 wherein $R_1$ is lower alkyl attached to position 2; and $R_2$ is selected from the group consisting of benzoyl, cinnamoyl, thionylcarbonyl, napthylcarbonyl, or furylcarbonyl substituted at the nitrogen on the indole ring.

30. A method according to claim 29 wherein $R_4$ is lower alkyl or lower alkyl at the 5-position on the indole ring.

31. The method according to claim 16 wherein said compound is administered orally.

* * * * *